(12) United States Patent
Kording et al.

(10) Patent No.: US 10,750,977 B2
(45) Date of Patent: *Aug. 25, 2020

(54) MEDICAL EVALUATION SYSTEM AND METHOD USING SENSORS IN MOBILE DEVICES

(71) Applicants: REHABILITATION INSTITUTE OF CHICAGO, Chicago, IL (US); NORTHWESTERN UNIVERSITY, Evanston, IL (US)

(72) Inventors: Konrad P. Kording, Chicago, IL (US); Mark V. Albert, Chicago, IL (US); Andrew Levien, Evanston, IL (US)

(73) Assignees: REHABILITATION INSTITUTE OF CHICAGO, Chicago, IL (US); NORTHWESTERN UNIVERSITY, Evanston, IL (US)

( * ) Notice: Subject to any disclaimer, the term of this patent is extended or adjusted under 35 U.S.C. 154(b) by 372 days.

This patent is subject to a terminal disclaimer.

(21) Appl. No.: 15/868,187

(22) Filed: Jan. 11, 2018

(65) Prior Publication Data

US 2018/0132756 A1 May 17, 2018

Related U.S. Application Data

(63) Continuation of application No. 13/642,219, filed as application No. PCT/US2011/033471 on Apr. 21, 2011, now Pat. No. 9,872,637.

(Continued)

(51) Int. Cl.
*A61B 5/00* (2006.01)
*A61B 5/11* (2006.01)
(Continued)

(52) U.S. Cl.
CPC .......... *A61B 5/1101* (2013.01); *A61B 5/1126* (2013.01); *A61B 5/4082* (2013.01);
(Continued)

(58) Field of Classification Search
CPC ..... A61B 5/1101; A61B 5/1126; A61B 5/117; A61B 5/4082; A61B 5/6898; G06F 19/3418; G06F 19/3431; G06F 19/3443
See application file for complete search history.

(56) References Cited

U.S. PATENT DOCUMENTS 7,244,231 B2 7/2007 Dewing et al.
7,248,172 B2 7/2007 Clifford et al.
(Continued)

FOREIGN PATENT DOCUMENTS

WO 01/65810 A1 9/2001
WO 02/09396 A2 1/2002
(Continued)

OTHER PUBLICATIONS

Brezmes et al., "Activity Recognition from Accelerometer Data on a Mobile Phone," IWANN 2009, Part II, LNCS 5518, 2009, pp. 796-799.

(Continued)

*Primary Examiner* — Max F Hindenburg
(74) *Attorney, Agent, or Firm* — Faegre Drinker Biddle & Reath LLP

(57) ABSTRACT

A medical evaluation system includes an I/O module, a processing module, and an analysis module. The I/O module receives sensory data obtained by a motion sensor disposed in a mobile device carried by a patient at least when the patient is in a non-clinical environment. The processing module extracts medically relevant data from the sensory data received from the sensor in the mobile device. The relevant data includes one or more features of interest in the (Continued)

sensory data. The analysis module derives one or more surrogate biomarkers from the relevant data. The surrogate biomarkers represent at least one of a state or a progression of a medical condition of the patient. The mobile device may be a mobile phone carried by the patient and the sensor may include at least one of an accelerometer or a gyroscope that generates the sensory data to represent movements of the patient.

33 Claims, 8 Drawing Sheets

Related U.S. Application Data

(60) Provisional application No. 61/342,930, filed on Apr. 21, 2010, provisional application No. 61/398,380, filed on Jun. 24, 2010.

(51) Int. Cl.
| | |
|---|---|
| *G06F 19/00* | (2018.01) |
| *G16H 50/30* | (2018.01) |
| *G16H 50/70* | (2018.01) |
| *G16H 40/67* | (2018.01) |

(52) U.S. Cl.
CPC .......... *G06F 19/00* (2013.01); *G06F 19/3418* (2013.01); *G16H 40/67* (2018.01); *G16H 50/30* (2018.01); *G16H 50/70* (2018.01); *A61B 5/6898* (2013.01)

(56) References Cited

U.S. PATENT DOCUMENTS

| | | | |
|---|---|---|---|
| 7,285,090 B2 | 10/2007 | Stivoric et al. | |
| 7,755,493 B2 | 7/2010 | Berenguer et al. | |
| 7,981,058 B2 | 7/2011 | Akay | |
| 8,187,209 B1 | 5/2012 | Giuffrida | |
| 8,821,414 B2 | 9/2014 | Moersdorf et al. | |
| 9,451,895 B2 | 9/2016 | Markel | |
| 9,872,637 B2 * | 1/2018 | Kording | G06F 19/00 |
| 2004/0147817 A1 | 7/2004 | Dewing et al. | |
| 2005/0124375 A1 | 6/2005 | Nowosielski | |
| 2005/0240086 A1 | 10/2005 | Akay | |
| 2006/0270949 A1 | 11/2006 | Mathie et al. | |
| 2006/0282021 A1 | 12/2006 | De Vaul et al. | |
| 2007/0033068 A1 | 2/2007 | Rao et al. | |
| 2008/0004904 A1 | 1/2008 | Tran | |
| 2008/0129518 A1 | 6/2008 | Calton-Foss | |
| 2009/0048493 A1 | 2/2009 | James et al. | |
| 2009/0204030 A1 | 8/2009 | Brauers et al. | |
| 2009/0326419 A1 | 12/2009 | Gonzalez Rojas et al. | |
| 2010/0169409 A1 | 7/2010 | Fallon et al. | |
| 2010/0268551 A1 | 10/2010 | McNames et al. | |
| 2010/0280335 A1 | 11/2010 | Carlson et al. | |
| 2011/0046519 A1 | 2/2011 | Raheman | |
| 2011/0098608 A1 | 4/2011 | Griffiths et al. | |

FOREIGN PATENT DOCUMENTS

| | | |
|---|---|---|
| WO | 2007/136677 A2 | 11/2007 |
| WO | 2009/006980 A2 | 1/2009 |
| WO | 2010/037564 A1 | 4/2010 |
| WO | 2010/126878 A1 | 11/2010 |
| WO | 2010/150260 A1 | 12/2010 |
| WO | 2011/133799 A1 | 10/2011 |

OTHER PUBLICATIONS

Dillow, "Cell Phone Accelerometer Tech Could Predict When a Horse Is About to Go Lame," 2010, retrieved from internet website: www.popsi.com/technology/article/2010-06/cell-phone-tech-could-diagnose-lameless-horses-earlier, on Jan. 7, 2013, 1 page.
Godfrey et al., "Direct measurement of human movement by accelerometry," Medical Engineering & Physics, 2008, vol. 30, pp. 1364-1386.
Heldman et al., "Automated Parkinson's Disease Motor Assessment for Clinical and Ambulatory Monitoring," CleveMed, 1 page.
Kwapisz et al., "Cell Phone-Based Biometric Identification," IEEE, 2010, 7 pages.
Ravi et al., "Activity Recognition from Accelerometer Data," IAAI-05, 2005, pp. 1541-1546.
Wu et al., "MEDIC: Medical embedded device for individualized care," Artificial Intelligence in Medicine, 2008, vol. 42, pp. 137-152.
Zhang et al., "Fall Detection by Embedding an Accelerometer in Cellphone and Using KFD Algorithm," IJCLNS International Journal of Computer Science and Network Security, Oct. 2006, vol. 10(6), pp. 277-284.
PCT Search Report and Written Opinion issued in related application PCT/US2011/033471, dated Jul. 11, 2011, 11 pages.

\* cited by examiner

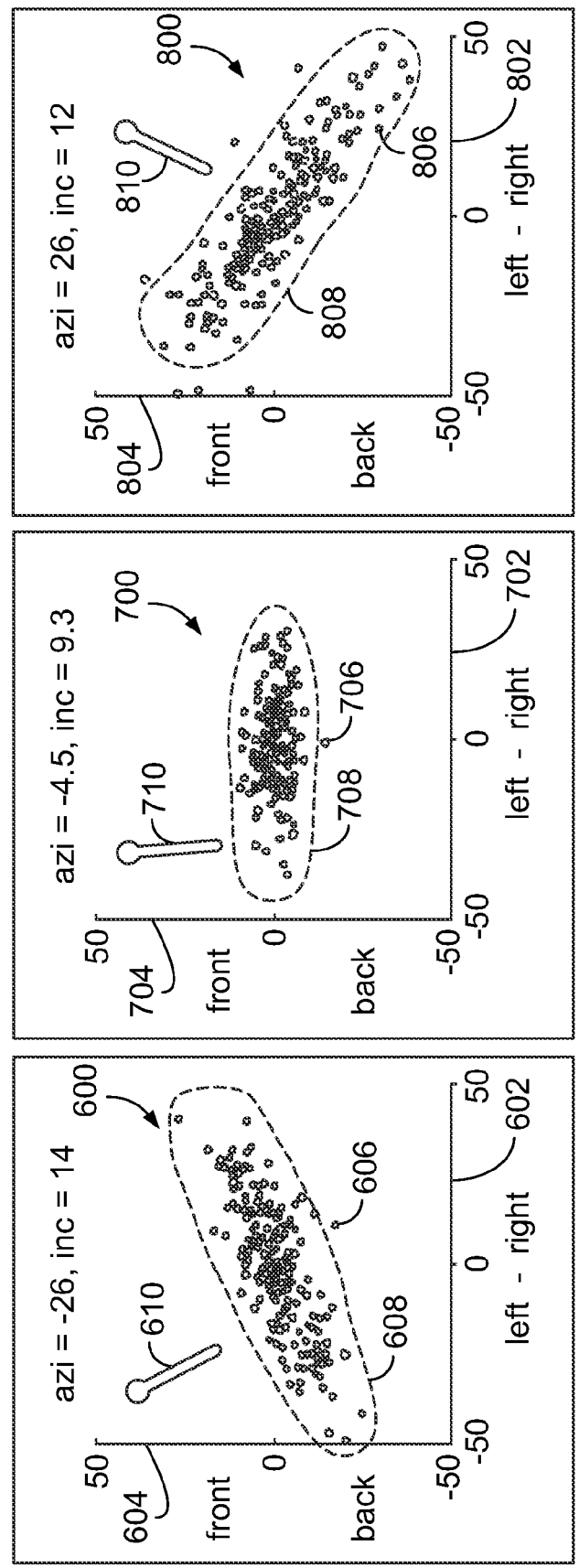

MEDICAL EVALUATION SYSTEM AND METHOD USING SENSORS IN MOBILE DEVICES

CROSS-REFERENCE TO RELATED APPLICATIONS

This application is a continuation of U.S. patent application Ser. No. 13/642,219 (the "'219 application"), filed on Oct. 19, 2012, now U.S. Pat. No. 9,872,637, which is a U.S. national stage entry of International Application No. PCT/US11/33471, which was filed on Apr. 21, 2011, and is entitled "Medical Evaluation System And Method Using Sensors In Mobile Devices" (the "'471 application"). The '471 application claims priority to U.S. Provisional Patent Application Ser. No. 61/342,930, which was filed on Apr. 21, 2010, and is entitled "Techniques For Determining And Applying Information Indicative Of Posture" (the "'930 application"). The '471 application also claims priority to U.S. Provisional Patent Application Ser. No. 61/398,380, which was filed on Jun. 24, 2010, and is entitled "Techniques For Detecting And Applying Information Relating To Movement Of A Subject" (the "'380 application"). The entire disclosures of the '219 Application, the '471 Application, the '930 Application, and the '380 application are incorporated by reference herein.

BACKGROUND

Patients suffering from a variety of diseases or other medical conditions receive medical treatment from physicians. Typically, a patient with a chronic disease must travel to the office of the physician, such as a hospital, clinic, or other medical setting (referred to herein as "clinical environments"), for check-ups with the physician. During the check-ups, the physician may perform a series of tests and examinations on the patient to monitor the progression of the disease. The physician may change one or more therapies or order diagnoses provided to the patient to correctly treat the disease based on the results of the tests and examinations. For example, the physician may change a medication, a dosage of a medication, order a test, and the like, based on the progression of the disease.

Medical decisions are generally limited by the amount of medical data that is available for examination. For example, typically the physician only has access to medical data that is obtained from the patient while the patient is in the clinical environment as well as self-reports by the patient. While the physician can have access to historical medical data, such as medical data obtained during previous visits to the physician, the total medical data available to the physician usually only represent a small fraction of the total time that the patient suffers from the disease.

The physician usually does not have access to medical data that is obtained when the patient is outside of the clinical environments, or may have limited access to such medical data. The cost and/or size of the equipment used by the physician to obtain medical data when the patient is in the clinical environment can be prohibitively expensive and/or large for a patient to take the equipment with him or her outside of the clinical environment.

As a result, the physician generally has a limited amount of data that is relevant to a patient's disease. While helpful, this medical data may not provide a complete enough picture of the disease state of the patient for efficient medical decision making. For example, the medical data usually does not contain information about the activities patients undergo during the day and how these activities are affected by drugs and disease. This also complicates the detection of changes or trends in the disease of the patient when the patient is outside of the clinical environment.

With the goal of improving patient outcomes while at the same time reducing patient care costs, the need exists for a system and method that can obtain and provide medical data of a patient and provide feedback to the patient all while the patient is outside of a clinical environment with equipment that is reasonable in cost and/or size.

BRIEF DESCRIPTION

Reference will be made below in detail to example embodiments of the inventive subject matter, examples of which are illustrated in the accompanying drawings. Wherever possible, the same reference numerals used throughout the drawings refer to the same or like parts.

In accordance with one embodiment, a medical evaluation system is provided. The system includes an I/O module, a processing module, and an analysis module. The I/O module is configured to receive sensory data obtained by a motion sensor disposed in a mobile device carried by a patient at least when the patient is in a non-clinical environment. The processing module is configured to extract medically relevant data from the sensory data received from the sensor in the mobile device. The relevant data includes one or more features of interest in the sensory data. The analysis module is configured to derive one or more surrogate biomarkers or other measures of interest from the relevant data using machine learning and pattern recognition techniques. The surrogate biomarkers represent at least one of a state or a progression of a medical condition of the patient.

In another aspect, the surrogate biomarkers may include one or more estimates of quantitative clinical scores for a rating system that monitors progression or severity of a disease state of the patient.

In another aspect, the mobile device is a mobile phone carried by the patient and the sensor includes at least one of an accelerometer or a gyroscope that generates the sensory data to represent movements of the patient.

In another aspect, the analysis module is configured to employ one or more machine learning algorithms that identify one or more patterns or trends in the relevant data to derive the surrogate biomarkers.

In another aspect, the surrogate biomarkers include an estimate of a quantitative clinical score in a medical ranking system.

In another aspect, the analysis module is configured to employ one or more machine learning algorithms that compare the relevant data of the patient with relevant data obtained from a sample of one or more other persons associated with different quantitative clinical scores in the rating system. The analysis module may determine the one or more estimates of quantitative clinical scores for the patient based on similarities or other statistical regularities between the relevant data of the patient and the relevant data of one or more of the persons in the sample.

In another aspect, the one or more estimates of quantitative clinical scores include at least one of an indication of early onset, a probability of early onset of a disease of the patient, or timing of early onset.

In another aspect, the system also includes an authentication module that is configured to determine one or more of the features of interest in the sensory data as the relevant data and use the relevant data to identify the patient carrying the mobile device using one or more machine learning algorithms or pattern recognition algorithms.

In another aspect, the authentication module is configured to determine a location that the mobile device is carried by the patient (e.g., which pocket) based on a comparison between the relevant data and one or more location signatures associated with the patient. The location signatures may include one or more of the features of interest of previously acquired sensory data from the sensor when the device is carried in different locations on the patient.

In another aspect, the analysis module is configured to transmit information that enables an intervention to the device based on one or more properties or changes in the relevant data. The intervention may include a notification communicated to the patient or health provider via the device or other means to change a current or future activity of the patient.

In another aspect, the I/O module is configured to transmit a report including the surrogate biomarker to one or more of a healthcare provider, an insurance company, a family member of the patient, or a friend of the patient.

In another embodiment, a method for monitoring a medical condition of a patient is provided. The method includes receiving the sensory data obtained from a motion sensor in a mobile device carried by a patient at least in a non-clinical or clinical environment and extracting the medically relevant data from the sensory data by identifying one or more features of interest in the sensory data. The method further includes deriving the surrogate biomarker from the relevant data, wherein the surrogate biomarker represents at least one of a state or a progression of the medical condition of the patient, using machine learning algorithms and/or other data analysis techniques.

In another aspect, the surrogate biomarker includes an estimate of one or more quantitative clinical scores of a rating system that monitors progression of a disease state of the patient.

In another aspect, the mobile device is a mobile phone carried by the patient and the sensor includes at least one of an accelerometer or a gyroscope that generates the sensory data to represent movements of the patient.

In another aspect, deriving the surrogate biomarker includes employing one or more machine learning algorithms that identify and compare the relevant data of the patient with relevant data obtained from a sample of one or more other persons associated with different quantitative clinical scores in the rating system.

In another aspect, deriving the surrogate biomarker includes employing one or more machine learning algorithms that compare the relevant data of the patient with relevant data obtained from a sample of one or more other persons associated with different quantitative clinical scores in the rating system. Deriving the surrogate biomarker may include selecting one or more quantitative clinical scores for the patient based on similarities or other statistical relations between the relevant data of the patient and the relevant data of one or more of the persons in the sample.

In another aspect, the surrogate biomarker includes at least one of an indication of early onset or a probability of early onset of a disease of the patient.

In another aspect, the method also includes determining one or more of the features of interest in the sensory data as the relevant data and using the relevant data to identify the patient carrying the mobile device.

In another aspect, the method also includes determining a location that the mobile device is carried by the patient based on a comparison between the relevant data and one or more location signatures associated with the patient. The location signatures may include one or more of the features of interest of previously acquired sensory data from the sensor when the device is carried in different locations on the patient.

In another aspect, the method also includes transmitting an intervention to the device based on one or more changes in the relevant data. The intervention may include a notification communicated to the patient via the device to change a current activity of the patient.

In another embodiment, a computer readable storage medium for a medical evaluation system having a processor is provided. The medium may be a tangible and non-transitory medium. The medium includes one or more sets of instructions that direct the processor to receive sensory data obtained by a motion sensor in a mobile device that is carried by a patient in a non-clinical environment or clinical environment and extract medically relevant data from the sensory data by identifying one or more features of interest in the sensory data. The sets of instructions also direct the processor to derive a surrogate biomarker from the relevant data, wherein the surrogate biomarker represents at least one of a disease state, an injury state, or a progression of a disease of the patient.

In another aspect, the sets of instructions direct the processor to derive the surrogate biomarker by estimating one or more quantitative clinical scores of a rating system that monitors progression of a disease state of the patient.

In another aspect, the mobile device is a mobile phone carried by the patient and the sensor includes at least one of an accelerometer or a gyroscope that generates the sensory data to represent movements of the patient.

In another aspect, the sets of instructions direct the processor to employ one or more machine learning algorithms that compare the relevant data of the patient with relevant data obtained from a sample of one or more other persons associated with different quantitative clinical scores in the rating system. The sets of instructions also direct the processor to select one or more the one or more quantitative clinical scores for the patient based on similarities between the relevant data of the patient and the relevant data of one or more of the persons in the sample.

In another aspect, the sets of instructions direct the processor to employ one or more machine learning algorithms that identify at least one of a pattern or a trend in the relevant data, and the surrogate biomarker is based on the at least one of the pattern or the trend.

In another aspect, the surrogate biomarker includes at least one of an indication of early onset or a probability of early onset of a disease of the patient.

In another aspect, the one or more sets of instructions direct the processor to determine one or more of the features of interest in the sensory data as the relevant data and identify the patient carrying the mobile device based on the features of interest.

In another aspect, the one or more sets of instructions direct the processor to determine a location that the mobile device is carried by the patient based on a comparison between the relevant data and one or more location signatures associated with the patient. The location signatures may include one or more of the features of interest of previously acquired sensory data from the sensor when the device is carried in different locations on the patient.

In another aspect, the one or more sets of instructions direct the processor to transmit an intervention to the device based on one or more changes in the relevant data. The intervention may include a notification communicated to the patient via the device to change a current activity of the patient.

In another embodiment, a medical evaluation system is provided. The system includes a device with built in sensors and a computation module that uses mathematical or computational techniques to convert the obtained data into clinically relevant data. The computation module is configured to receive sensory data coming from a sensor that is carried by a patient. By way of example, the sensor may be disposed inside a mobile phone carried by the patient. The sensory data are obtained by the device, but usually in a location different from the computational module. For example, the sensory data may be obtained when the patient is at home, work, school, or another environment other than a hospital or other medical facility. The computational module is configured to analyze the sensory data and convert it into data of interest. One example would be surrogate biomarkers of movement. Another would be a positive progression or a negative progression in a disease state of the patient. In one aspect, the sensor is a motion sensor that generates movement data based on motion of the patient. The system may include a processing module configured to examine the movement data and identify one or more movement activities or activity transitions between movement activities that the patient engages in when the movement data is obtained.

In another embodiment, a method for monitoring surrogate biomarkers of a patient is provided. The method includes receiving the surrogate biomarkers obtained by a sensor disposed in a mobile phone carried by the patient when the patient is in a non-clinical environment. The method also includes analyzing the surrogate biomarkers obtained when the patient is in the non-clinical environment to identify one or more trends in the surrogate biomarkers over time. The method further includes providing a recommended change to a therapy provided to the patient in connection with treatment of a disease. The recommended change is based on the one or more trends in the surrogate biomarkers. In one aspect, analyzing the surrogate biomarkers may include comparing one or more of the biomarkers obtained in the non-clinical environment prior to a change in the therapy with one or more of the biomarkers obtained in the non-clinical environment after the change in the therapy.

At least one technical effect of the subject matter described herein is the output of a digital signal that includes surrogate biomarkers to a healthcare provider, such as a physician. The surrogate biomarkers include clinically relevant information that is derived from machine learning analysis and/or pattern recognition analysis of sensory data provided by a motion sensor in a mobile device carried by a patient. The healthcare provider can use the surrogate biomarkers to diagnose a disease of the patient, modify a therapy and/or medication provided to the patient, and/or track a progression of the disease of the patient.

BRIEF DESCRIPTION OF THE DRAWINGS

The subject matter described herein will be better understood from reading the following description of non-limiting embodiments, with reference to the attached drawings, wherein below:

FIGS. 8 through 10 are examples of displacement data;

DETAILED DESCRIPTION

Figure 1:
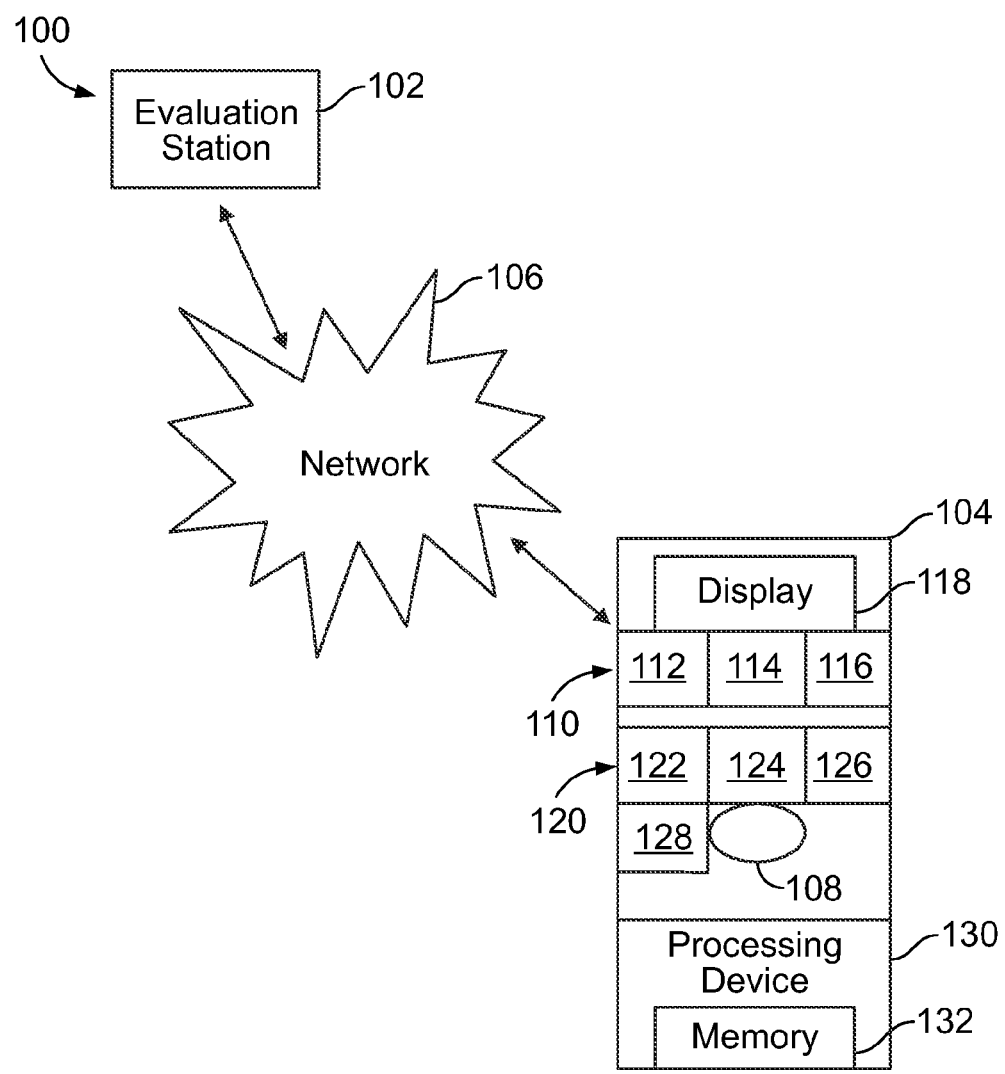
FIG. 1 is a schematic diagram of one embodiment of a medical evaluation system.

In accordance with one or more embodiments described herein, a medical evaluation system and method are provided. A mobile device that is carried by a patient acquires sensory data. The sensory data represents movements of the patient. The sensory data is examined and/or analyzed to extract medically relevant data from the sensory data. For example, the sensory data may be analyzed using computer-implemented machine learning algorithms that extract relevant data from the sensory data. The relevant data can include measurements of an amount of movement of the patient. For example, the relevant data can include measurements of a magnitude, frequency, and/or duration of tremors of the patient. The relevant data can be analyzed by computer-implemented machine learning algorithms and/or computer-implemented pattern detection algorithms to derive surrogate biomarkers from the relevant data.

Surrogate biomarkers represent clinically relevant information that is of interest to a healthcare provider in monitoring or determining a severity of disease or injury. For example, a surrogate biomarker may be a quantity that represents a negative or positive progression in a disease state of the patient. The algorithms that derive the surrogate biomarkers from the relevant data may examine the relevant data to determine medically relevant patterns, trends, or changes in the relevant data. A surrogate biomarker that is a pattern can be a temporal pattern of features of interest of the relevant data (e.g., the occurrence of two or more features of interest at relative times). In another example, a surrogate biomarker is a posture of the patient that is derived from a pattern of tremors or other movements of the patient. In another example, a surrogate biomarker can be a trend in the relevant data, such as an increase or decrease in one or more features of interest in the relevant data over time. As another example, a surrogate biomarker can include an estimate of a quantitative clinical score or measure for a scale or rating system that monitors progression or state of a patient's condition or disease. For example, surrogate biomarkers can include estimates of Functional Independence Measures (FIMs) and/or Universal Parkinson's Disease Rating Score (UPDRS).

The sensory data can be obtained by sensors that are present in a mobile phone typically carried by the patient throughout the daily life of the patient. For example, the sensory data can be collected when the patient is in non-clinical environments, such as locations where the patient is not being examined by his or her physician. Examples of non-clinical environments can include the home environment of the patient, the work environment of the patient (even if the patient works in a clinical environment, but including those time periods when the patient is not being examined by a physician), a school, or other locations that the patient may encounter in his or her daily life. The sensory data also can be obtained when the patient is in clinical environments, such as clinics, hospitals, and other locations where the patient is being examined and/or treated by one or more healthcare professionals. Using a mobile phone or other device that is carried by the patient throughout the daily life of the patient can provide the ability to collect the sensory data in a continuous or near-continuous manner. For example, the sensory data can be obtained for a majority (e.g., more than 12 hours) of the day when the patient has the mobile phone with him or her. The sensory data may be obtained over a period of several days or weeks or more to monitor the patient and/or changes in a disease state of the patient.

FIG. 1 is a schematic diagram of one embodiment of a medical evaluation system 100. The system 100 includes an evaluation station 102 that communicates with a communication/sensing device 104 via one or more networks 106. The evaluation station 102 may include one or more processing devices, such as one or more interconnected computers or computer servers, that are remotely located from the device 104. For example, the evaluation station 102 may be located in a different room, different floor, different building, different city block, different Zone Improvement Plan (ZIP) code (or other geographic-based code), different town or city, different county, different state, and/or different country than the device 104. The network 106 can represent one or more computer networks capable of communicating data. For example, the network 106 can include all or part of the Internet, one or more intranets, cellular networks (e.g., EDGE, 3G, 4G networks, and the like), and/or one or more other private and/or public networks.

In one embodiment, the device 104 is a portable or handheld device that includes one or more sensors that generate sensory data based on detected characteristics of the patient carrying the device 104. The device 104 may be a portable communication device, such as a mobile or cellular phone, in one embodiment. For example, the device 104 may be a personal digital assistant (PDA), mobile phone, or other relatively small computing device, that includes capabilities to perform wireless telephonic and/or data communications over the network 106 with other phones, computers, mobile phones, and the like. Nonlimiting examples of the device 104 may include the IPHONE of Apple Computers, a mobile phone running an ANDROID operating system, a BLACKBERRY device, a PALM PRE device, or a WINDOWS mobile phone. Alternatively, the device 104 may be a portable communications device that communicates data through the network 106 without providing for telephonic communications with one or more other devices.

The device 104 is a portable or handheld device in that the device 104 may be hand carried by a patient of average size and strength, fixed to an appendage or other portion of the body of the patient (e.g., strapped to an appendage, belt, or waistline of the patient), and/or carried in a clothes pocket (e.g., a shirt pocket, a pocket of a jacket, coat, sportcoat, or suit, a back or front pants pocket, and the like) of the patient. The device 104 may include one or more output devices 110, such as a visual display 118, a loudspeaker 112, an audio out interface or jack 114, and/or one or more other communication interfaces 116. The device 104 can include one or more input devices 120, such as a keypad 122, a cursor control device 124, and/or a microphone 126. In one embodiment, the visual display 118 ("display") may be a touch sensitive screen (e.g., touchscreen) that can receive touches from the patient as input to the device 104. The device 104 includes one or more sensors, such as a Global Positioning System (GPS) receiver 128 and/or a sensor 108.

The sensor 108 can include a device capable of generating sensory data that represents motions of the patient. For example, the sensor 108 may be a motion sensor that includes an accelerometer and/or gyroscope to measure motion of the patient. In one embodiment, the sensor 108 is a sensor that includes a single or multiple axis accelerometer or gyroscope. The sensor 108 can generate data signals representative of detected acceleration of the device 104 along one or more axes. The sensor 108 may include a gyroscope that generates data signals representative of detected motion along one or more axes. Alternatively, the sensor 108 may represent one or more other devices that generate data signals based on movement of the device 104, such as a switch, force sensor, position sensor, velocity sensor, or the like. In one embodiment, the sensor 108 may measure micromovements of the patient as the motions. Micromovements can include motions of the patient that are relatively small motions, such as heart contractions during cardiac cycles, respirations, and the like.

The sensor 108 may be a preexisting sensor of the device 104. By "preexisting," it is meant that the sensor 108 in the device 104 is included in the device 104 when the device 104 is first purchased or acquired by the patient and is not added as an external and/or after-market addition to the device 104. Alternatively, the sensor 108 may be added to the device 104 of the patient after the patient has purchased or otherwise first acquired the device 104. For example, the sensor 108 may be an after-market sensor.

In another embodiment, the sensor 108 may not be disposed in the mobile device 104. For example, the sensor 108 may be external to mobile devices and capable of acquiring sensory data representative of motions of the patient. As one example, the sensor 108 may be a camera or other optical arrangement that detects motion of a patient using captured videos and/or images.

The sensor 108 may acquire sensory data in a continuous or near-continuous manner. For example, the sensor 108 may acquire sensory data representative of motion of the patient periodically throughout the entire day that the patient is carrying the device 104 and/or at least a majority of the day. The sampling frequency of the sensor 108 may vary based on the types of sensory data sought to be obtained. For example, if the sensor 108 is acquiring sensory data representative of movements of the patient, then the sensor 108 may use different sampling frequencies or rates for different activities. In one embodiment, a sampling frequency of at least 10 hertz is used. Alternatively, a different frequency may be used.

The device 104 includes a data processing device 130 ("processing device 130") that operates to execute operating logic to perform one or more operations. For example, the processing device 130 may include one or more computer processors that operate based on one or more sets of instructions. The sets of instructions can include one or more software applications or programs stored on a computer readable storage medium 132 ("memory"). The memory 132 may be a tangible and non-transitory computer readable storage medium such as a solid-state, electromagnetic, and/or optical memory. The memory 132 can be volatile, non-volatile, or a mixture thereof. Some or all of the memory 132 can be portable, such as a disk, card, memory stick, cartridge, and the like.

The processing device 130 can include appropriate signal conditioners to transmit and receive desired information (e.g., data), and correspondingly may include filters, amplifiers, limiters, modulators, demodulators, CODECs, signal formal converters (such as analog-to-digital and digital-to-analog converters), clamps, power supplies (e.g., battery), power converters, and the like, as needed to perform various control, communication, evaluation, and processing operations described herein. The processing device 130 can be comprised of one or more components of any type suitable to process input signals and provide desired output signals. Such components may include digital circuitry, analog circuitry, or a combination of both. The processing device 130 can be of a programmable type; a dedicated, hard-wired state machine; or a combination of these; and can further include multiple processors, arithmetic-logic units (ALUs), central processing units (CPUs), or the like. For forms or the processing device 130 with multiple processing units, distributed, pipelined, and/or parallel processing can be utilized.

In operation, motion of a patient carrying the device 104 is detected by the sensor 108, and corresponding sensory data representative of the motion may be prepared and/or stored in the memory 132 under supervision or direction of operating logic executed by the processing device 130. The sensory data may be provided to the evaluation station 102 via the network 106 for analysis. As described below, the evaluation station 102 may include one or more processing devices that apply computer-implemented machine learning algorithms and/or computer-implemented pattern recognition algorithms to extract medically relevant data from the sensory data and to derive surrogate biomarkers that represent progressions in a disease or injury state of the patient. In another embodiment, at least some of the extracting the relevant data from the sensory data and/or deriving the surrogate biomarkers from the relevant data may be performed by the device 104 and/or shared between multiple processors other than by the processing device 130 and/or the evaluation station 102.

Figure 2:
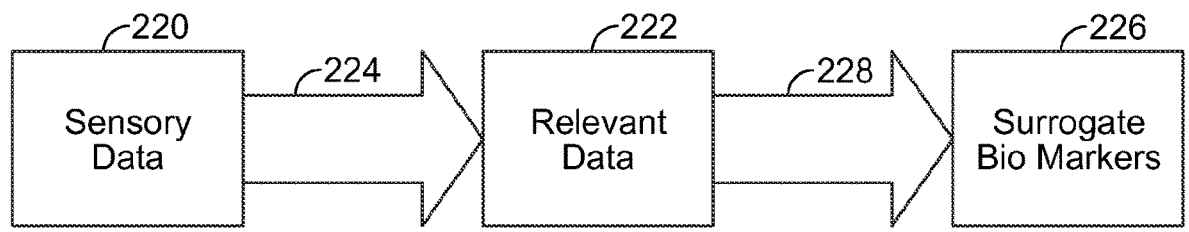
FIG. 2 is a schematic diagram of the flow and analysis of information in the system shown in FIG. 1.

FIG. 2 is a schematic diagram of the flow and analysis of information in the system 100 shown in FIG. 1. As described above, sensory data 220 is obtained by the sensor 108 (shown in FIG. 1). The sensory data 220 can represent raw data that is not processed or analyzed by the sensor 108 prior to the device 104 (shown in FIG. 1) transmitting the sensory data 220 to the evaluation station 102 (shown in FIG. 1). For example, the sensory data 220, or the quantities or characteristics represented by the sensory data 220, may not be altered by the device 104 other than for preparing the sensory data 220 for transmission to the evaluation station 102 (e.g., packetizing the sensory data 220 for transmission in a packet-switched network 106 shown in FIG. 1).

The sensory data 220 can be obtained when the patient is in a non-clinical environment, such as when the patient is at work, home, school, and the like and not being examined by a physician. Alternatively or in addition to the above, the sensory data 220 can be obtained when the patient is being examined by a physician. For example, under the supervision of a physician, the patient can hold the device 104 (shown in FIG. 1) in his or her hand while attempting to not move or move as little as possible in order to measure steady arm tremor of the patient. The sensor 108 (shown in FIG. 1) can record accelerations and/or other movements while the patient is doing so as the sensory data 220. As another example, the patient can hold the device 104 in his or her hand under the supervision of a physician and attempt to touch his or her nose with the device 104. As the patient moves to touch his or her nose, the sensor 108 obtains sensory data 220 of movements that may represent tremors of the patient. In another example, the patient may be instructed by the physician to put one foot in front of the other foot and stand still. The sensor 108 can obtain sensory data 220 that represents how much residual movement of the patient occurs while attempting to stand still. The device 104 may be attached to the patient and the physician may push or pull the patient while the sensor 108 records sensory data 220 of motions of the patient as the patient attempts to return to a standing still position.

The sensory data 220 is examined to identify medically relevant data 222. For example, one or more computer-implemented algorithms 224 may examine the sensory data 220 to identify one or more characteristics of interest from the sensory data 220 as the relevant data 222. "Machine learning" can include software algorithms that examine the sensory data 220 to identify features of interest in the sensory data 220. A feature of interest can include a quantity measured or calculated from the sensory data 220. Examples of features of interest include frequencies of the sensory data 220, time periods of the sensory data 220 (e.g., how long a section of the sensory data 220 lasts), magnitudes of the sensory data 220, and the like. The features of interest can represent characteristics of the sensory data 220 that distinguish the sensory data 220 of a first patient performing a first activity from sensory data of a second, different patient performing a second, different activity. A variety of machine learning techniques or algorithms may be used, including, but not limited to, support vector machines, neural networks, neuro-fuzzy systems, boosting, Bayesian learning, regression (e.g., regularized regression and/or regularized logistic regression), lasso, clustering, representation learning, and the like.

Additional examples of the relevant data 222 that is determined by the algorithms 224 can include an average tremor in a selected frequency range and/or temporal range of the sensory data 220. For example, the relevant data 222 can include an average magnitude of measured acceleration along one or more axes at a frequency and/or within a time window selected by a physician. As another example, the relevant data 222 can include a deviation from steady behavior. For example, the relevant data 222 can represent a measurement of accelerations that deviate from a motionless or substantially still patient.

In another example, the relevant data 222 can include a number, average, or median count of a particular good or poor behavior. Such relevant data 222 can include a number of times that the patient exercises, stops walking, or starts or stops other movement within a time window selected by a physician. As another example, the relevant data 222 can include an average or median activity level of the patient. An activity level of the patient can represent an amount of acceleration or other motion along one or more axes. The relevant data 222 can include a measured amount of sway of the patient. For example, the relevant data 222 can include measurements representative of a magnitude, frequency, and/or duration of residual movement of a patient. The sensory data 220 can obtained when the patient is holding the device 104 (shown in FIG. 1) in his or her hand and while attempting to not move. This sensory data 220 can be examined to determine the associated relevant data 222 that represents residual movement.

The relevant data 222 may include one or more parameters that describe recovery of the patient from a perturbation. For example, the relevant data 222 can include an average, median, or other statistical measure of a magnitude, frequency, and/or duration of movement by the patient along one or more axes after the patient stumbles. Alternatively, the relevant data 222 can include one or more other measures or portions of the sensory data 222 that may otherwise be evaluated non-quantitatively in clinical practice and that relates to movement. For example, the relevant data 222 can provide quantitative measurements of information that may otherwise be qualitatively examined by a physician.

As described below, the relevant data 222 can include an identity of the patient who generated the sensory data 220 from which the relevant data 222 is based. For example, the sensory data 220 may be examined to determine which of a plurality of patients that the sensory data 220 is associated with. In one embodiment, the relevant data 222 may include a location of the device 104 on the patient. For example, the relevant data 222 may represent where the device 104 is carried on the patient when the sensory data 220 is acquired by the sensor 108 (shown in FIG. 1).

The relevant data 222 is analyzed to derive surrogate biomarkers 226 relevant to the disease or injury state of the patient. For example, one or more computer-implemented algorithms 228 may examine the relevant data 222 to determine summaries, analyses, activities, trends, patterns, and other medically relevant information that is of interest to a healthcare provider in monitoring or determining a severity of disease or injury. For example, the surrogate biomarker 226 may be a quantity that represents a negative or positive progression in a disease state of the patient. The algorithms 228 can include computer-implemented machine learning algorithms and/or computer-implemented pattern recognition algorithms that examine the relevant data to determine medically relevant patterns, trends, or changes in the relevant data. The surrogate biomarkers 226 can include a temporal pattern of features of interest of the relevant data 222, a posture of the patient that is derived from a pattern of tremors or other movements of the patient, a trend in the relevant data 222, an estimate of a quantitative clinical score or measure for a scale or rating system that monitors progression or state of a patient's condition or disease, and the like. Additional examples of surrogate biomarkers 226 can include summaries of the relevant data 222 and/or changes in the relevant data 222, such as summaries of the percentage, ratio, or other fractions of time that the patient is active and/or sedentary, the average, median, or other statistical analysis of accelerations of the patient, the average, median, or other statistical analysis of movement cycles of the patient, and the like.

The algorithms 228 may include machine learning algorithms that adapt over time based on the relevant data 222 to determine the surrogate biomarkers 226. For example, the algorithms 228 may survey relevant data 222 obtained from a sample of other patients or persons (e.g., patients and/or healthy control persons) and/or video recordings of the other patients or persons. The relevant data 222 from the sample may be associated with known activities and/or disease states of the patients and other persons in the sample. For example, the relevant data 222 of the sample can be associated with different time periods of the other patients or persons when the other patients or persons are walking, running, driving or sitting in a moving vehicle such as a wheelchair, stumbling, resting, and the like. The algorithms 228 may examine the relevant data 222 from the sample and identify similarities between the relevant data 222 of a patient and the relevant data 222 from the sample. The similarities may be expressed as matches between features of interest of the sensory data 220. For example, magnitudes of tremors, temporal durations of tremors, frequencies of tremors, and the like, may be features of interest that are relevant data 222 and that can be compared from a patient to the same or similar features of interest of other patients in the sample. The different patients in the sample may be associated with different surrogate biomarkers 226. For example, different relevant data 222 may be associated with different patients in the sample who are in varying stages or progressions of a disease such as Parkinson's disease. If the quantitative values of the features of interest for the patient and for one or more patients in the same are within predetermined limits, then the surrogate biomarkers 226 associated with the one or more patients in the sample may also be associated with the patient.

Based on such similarities between the relevant data 222 of the patient and the relevant data 222 of patients in the sample, the algorithms 228 may identify a variety of surrogate biomarkers 226 for the patient, such as deviation of the relevant data 222 of the patient from the average, median, or other statistical measure of the relevant data 222 of the patients in the sample. As another example comparisons between the acceleration levels of the patient and the patients in the sample based on activity types may be surrogate biomarkers.

As described above, the surrogate biomarkers 226 can include estimates of quantitative clinical measures or scores of patient functionality and/or health. For example, the surrogate biomarkers 226 can include estimates of FIMs (Functional Independence Measures) and/or UPDRS (Universal Parkinson's Disease Rating Score). The estimates of such clinical scores or measures for a patient can be based on comparisons between the relevant data 222 of the patient with the relevant data 222 of a sample other patients or persons having known scores or measures. Similar to as described above, similarities between the relevant data 222 of the patient and the relevant data 222 of one or more persons in the sample may be used to estimate a quantitative clinical measure or score of the patient from known measures or scores of persons in the sample having similar relevant data 222.

In one embodiment, the surrogate biomarkers 226 can include an indication of early onset and/or a probability of early onset of one or more diseases. For example, the surrogate biomarkers 226 can include a notice indicating that the patient is exhibiting signs of the early onset of a disease, such as Parkinson's disease. In order to determine such surrogate biomarkers 226 for a patient, the algorithms 228 can apply machine learning techniques to compare the relevant data 222 of the patient with the relevant data 222 of a sample of other persons at various stages of one or more diseases, such as Parkinson's disease. Based on similarities or differences between the relevant data 222 of the patient and the relevant data 222 of the persons in the sample, the algorithms 228 may identify which of the persons in the sample have relevant data 222 that is more similar to the relevant data 222 of the patient than other patients in the sample. For example, the algorithms 228 may identify one or more persons having at least a threshold number or percentage of features of interest from the sensory data 220 that are the same or within a threshold range as the features of interest in the sensory data 220 of the patient. Based on which persons in the sample have the similar relevant data 222, the patient may be identified as being in the same state of early onset as the persons in the sample. This same state of early onset can be provided to the patient and/or physician as a surrogate biomarker 226.

Figure 3:
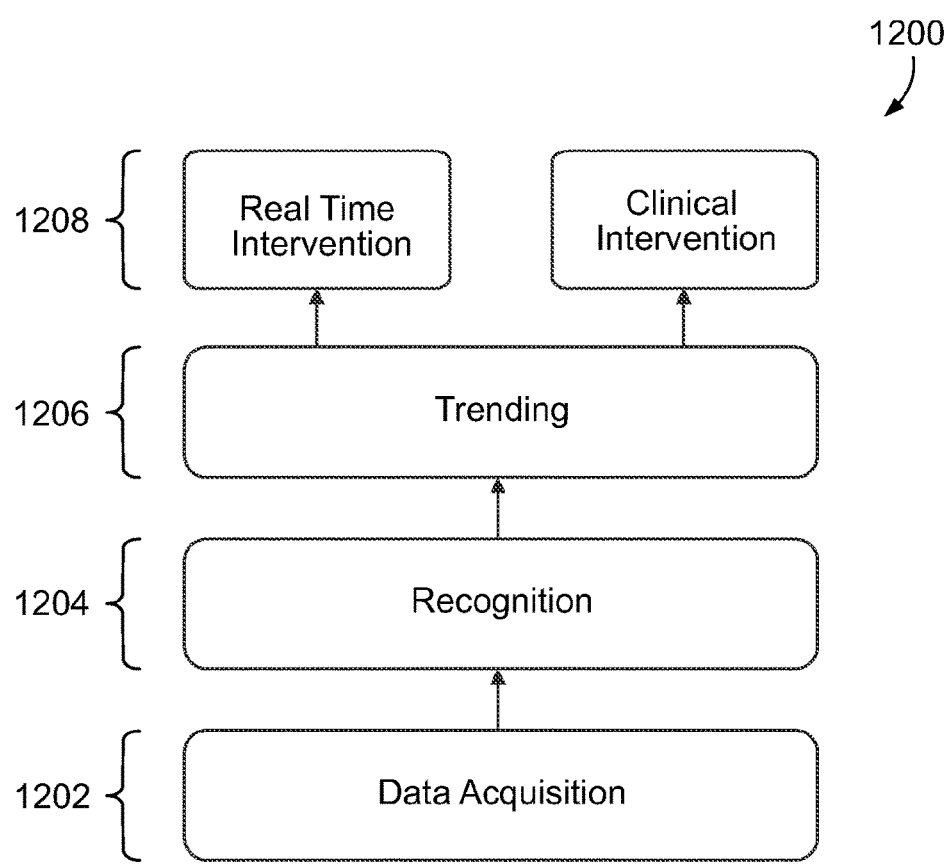
FIG. 3 is a schematic of a data analysis hierarchy in accordance with one embodiment.

FIG. 3 is a schematic of a data analysis hierarchy 1200 in accordance with one embodiment. The hierarchy 1200 visually represents various levels or operations of data acquisition and analysis, as described below. The hierarchy 1200 may include the use of one or more computer-implemented machine learning techniques or algorithms to sensory data that represents motion of a patient and the multiple outputs of applying these techniques or algorithms to the sensory data. Examples of such outputs can include identified postures of the patient and other surrogate biomarkers that may be combined to provide a plurality of applications of relatively high practical value in a healthcare setting. Using the outputs and/or other surrogate biomarkers can improve outcomes for the patient while reducing healthcare costs.

The hierarchy 1200 can begin at a first level 1202, which is referred to as a data acquisition level. In the first level 1202, the sensory data described above is acquired by the device 104 (shown in FIG. 1). Additionally, the sensory data may be arranged into data packets for transmission to the evaluation station 102 (shown in FIG. 1). In one embodiment, error checking may be performed on the sensory data to prevent erroneous data (e.g., null data or other data that does not represent motion of the patient) from being transmitted to the evaluation station 102.

The next level of the hierarchy 1200 includes a second level 1204, which can be referred to as a recognition level. At the recognition level, the sensory data is examined to determine relevant data that can be used to detect which patient is being tracked (e.g., identity authentication), which pocket the device 104 (shown in FIG. 1) is being carried in (or otherwise where on the patient the device 104 is located), and/or which location the patient is located in (e.g., predefined zones of prevalent physical location like home, work, among others). For example, the GPS receiver 128 (shown in FIG. 1) of the device 104 may be used to determine the geographic location of the patient. The geographic location of the patient may be associated with the surrogate biomarkers derived for the patient. For example, the patient may be associated with a plurality of different locations, such as geofences that correspond to different environments, such as the home of the patient, the work place of the patient, the school of the patient, and the like. The GPS receiver 128 can determine when the patient is in one or more of these geographic locations and the surrogate biomarkers can be associated with the geographic locations. For example, surrogate biomarkers that are derived from sensory data and relevant data obtained when the patient is at home can be differentiated from surrogate biomarkers that are derived from sensory data and relevant data obtained when the patient is in another location. Associating the surrogate biomarkers with the locations at which the sensory data was acquired can assist healthcare providers in monitoring the medical condition of the patient as the activities of the patient may vary based on the different locations.

The next level of the hierarchy 1200 includes a third level 1206, which is referred to as a trending level. In the trending level, the sensory data and/or relevant data is examined to identify activities and movements of the patient and/or trends of changes in the activities and movements. The recognition of activities (e.g., identification of walking, sitting, standing, or background tremors) and the recognition of activity transitions (e.g., changing from sitting to standing) may be followed by application of statistical and machine learning analysis of the activities and activity transitions to identify trends, or changes in the activities or activity transitions that may be a result of factors such as fatigue, time of day, stress, medication, disease progression, or patient training.

Use of the machine learning techniques can give rise to surrogate biomarkers within each of these activities and transitions that are statistically equivalent or similar measures of patient functionality and health such as FIMs (Functional Independence Measures) and UPDRS (Universal Parkinson's Disease Rating Score). For example, FIM is a quantitative clinical score on a scale that assesses physical and/or cognitive disability. UPDRS is a quantitative clinical score used to track progression of Parkinson's disease. Other quantitative clinical scores and measures may be used. In one embodiment, the surrogate biomarkers that are derived from the sensory data and the relevant data can be used as estimates of quantitative clinical scores or measures, such as estimates of FIMs and/or UPDRS. These surrogate biomarkers that represent patient functionality can be based off of sensory data acquired when the patient is in a clinical environment and/or outside of a clinical environment from sensory data from the device 104. The ability to obtain the surrogate biomarkers when the patient is in and/or outside of a clinical environment can provide for real time assessment of the health of a patient while the patient is in his or her natural environment. Additionally, the surrogate biomarkers can provide valuable insight to true functionality of the patient outside of the clinical environment. In addition to determining real time data on activities and activity transitions, in one embodiment, reporting of the activities, activity transitions, and/or surrogate biomarkers is made available to healthcare providers and payers to assist in the long term tracking and assessment of patient medication and therapy outcomes. In the case of the payers, this reporting could also be used for automated performance-based payment methods using improvements in the FIMs or UPDRS derived from the surrogate biomarkers.

The next level of the hierarchy 1200 includes a fourth level 1208, which can be referred to as an intervention level. The intervention level can build on the outputs of one or more of the first through third levels 1202, 1204, 1206 and may provide real time and/or clinical interventions either directly to the patient (in the case of real time interventions) or indirectly through the healthcare provider in the case of the clinical interventions. For example, a real time intervention can use changes in surrogate biomarkers representative of activities of the patient to trigger cueing to the patient via the device 104 (shown in FIG. 1) to change gait or posture as a reinforcement to a clinical training of the patient. Such cueing can improve the efficacy of training provided to the patient. The cueing can involve sending a notification to the device 104 in real time, or in a relatively short time period following detection of an activity (e.g., within a few seconds or minutes). A clinical intervention can be provided to a healthcare provider, such as a physician, and/or the patient when values of one or more surrogate biomarkers (such as posture and/or gait) approach danger levels or thresholds. The clinical intervention can include a fall prevention alarm that is sent to the device 104 and that suggests that the patient cease the current activity, contact a third party for assistance, and the like. The clinical intervention also may be sent to the healthcare provider. The potential of reducing a statistically significant number of falls may have a significant impact on outcomes and cost in preventing significant pain, suffering, and injury. Other clinical interventions can include recognizing patterns of change in the surrogate biomarkers to suggest medication changes or therapeutic training regimens. In one embodiment, an intervention may be provided in the form of an alarm sent to emergency personnel and/or one or more predesignated family members or friends to notify the recipients of the alarm of an event, such as the patient falling or exhibiting signs of a problematic state (e.g., a long period of no detected movement).

Figure 4:
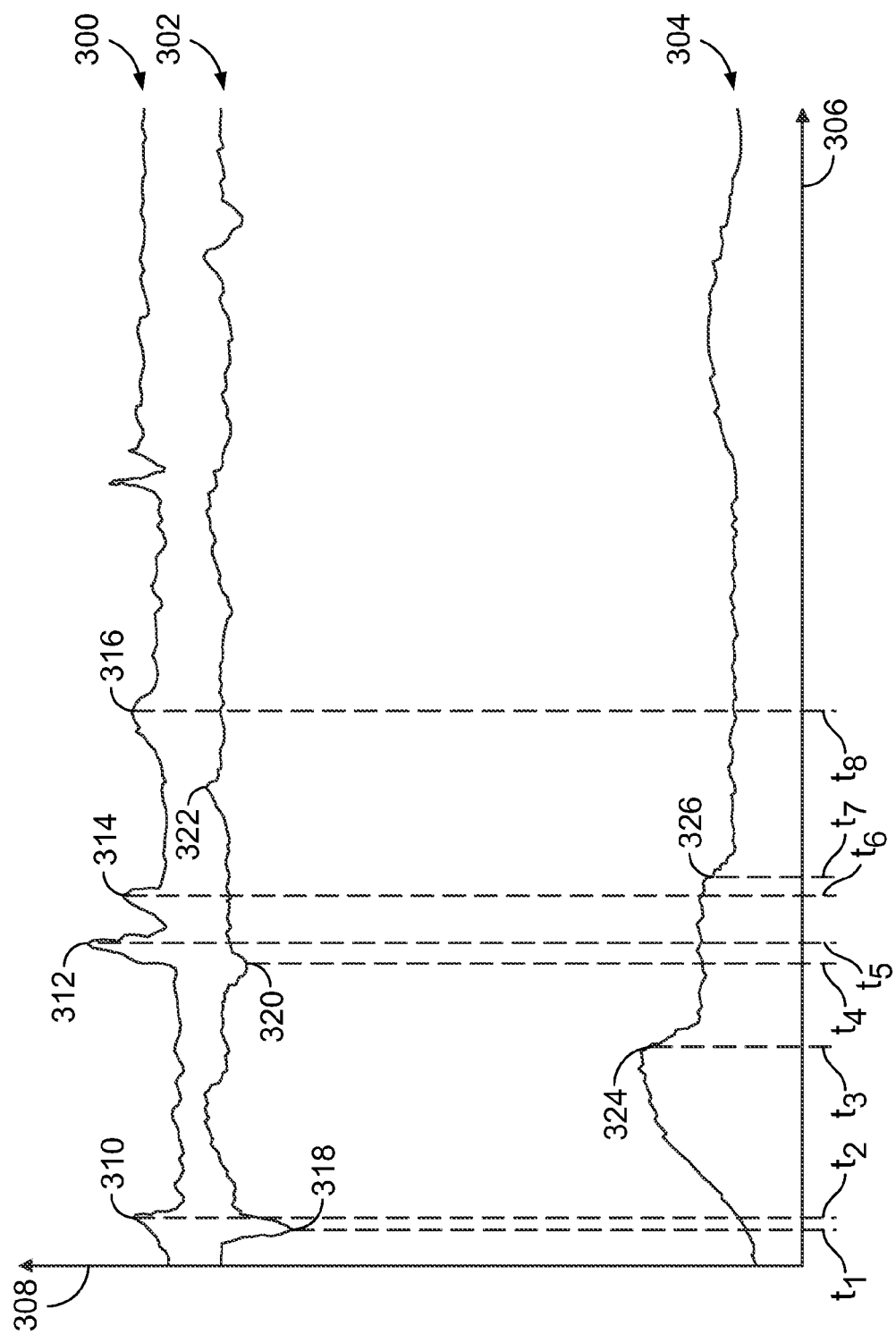
FIG. 4 is one example of sensory data obtained by a sensor of a mobile device (shown in FIG. 1)

FIG. 4 is one example of sensory data 300, 302, 304 obtained by the sensor 108 (shown in FIG. 1). The sensory data 300, 302, 304 is shown alongside a horizontal axis 306 that represents time and a vertical axis that represents acceleration. The sensory data 300, 302, 304 may be a time-domain representation of accelerations measured by the sensor 108 (shown in FIG. 1) in three mutually orthogonal directions over a period of time for the patient. Alternatively, the sensor 108 may measure accelerations along a different number of axes and/or non-orthogonal axes. The sensory data 300, 302, 304 is provided merely as an example of accelerations that may be used by the system 100 in various manners, as described below. When the patient carrying the device 104 (shown in FIG. 1) moves, the sensor 108 measures accelerations or other movement along one or more axes and records the accelerations or other movements as the sensory data 300, 302, 304.

Figure 5:
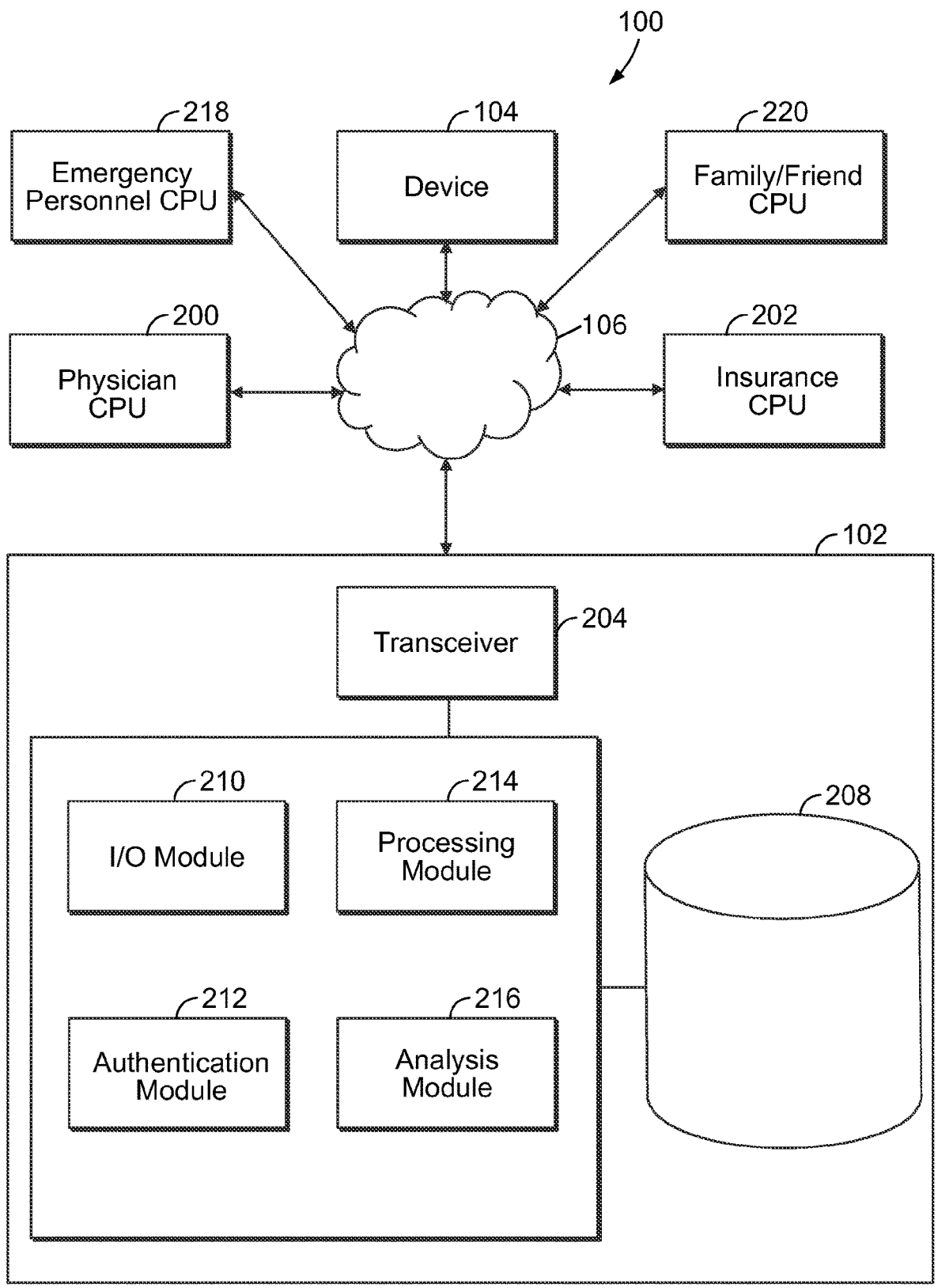
FIG. 5 is another schematic diagram of one embodiment of the medical evaluation system.

FIG. 5 is another schematic diagram of one embodiment of the medical evaluation system 100. As shown in FIG. 5, the evaluation station 102 can communicate with the device 104 and one or more computing devices, such as a physician computing device 200 ("physician CPU"), an insurance company computing device 202 ("insurance CPU"), an emergency personnel computing device 218 ("emergency personnel CPU"), a computing device of a family member and/or friend of the patient 220 ("family/friend CPU"), and the like. The evaluation station 102 can communicate with the additional computing devices 200, 202, 218, 220 via the network 106. In the illustrated embodiment, the evaluation station 102 includes a transceiver 204 that is communicatively coupled with a processor 206 by one or more wired and/or wireless connections. The transceiver 204 transmits data from the evaluation station 102 to one or more of the device 104 and/or the computing devices 200, 202, 218, 220 and may receive sensory data from the device 104 and/or the computing devices 200, 202, 218, 220. The computing devices 200, 202, 218, 220 may be embodied in one or more desktop or laptop computers, mobile phones, personal digital assistants, tablet computers, and the like.

The processor 206 operates to execute operating logic to perform one or more operations. For example, the processor 206 may include one or more computer processors that operate based on one or more sets of instructions. The sets of instructions can include one or more software algorithms, applications, or programs stored on a computer readable storage medium 208 ("memory 208"). For example, one or more of the algorithms 224, 228 (shown in FIG. 2) may reside on the memory 208 and direct operations of the processor 206. The memory 208 may be a tangible and non-transitory computer readable storage medium such as a solid-state, electromagnetic, and/or optical memory. The memory 208 can be volatile, nonvolatile, or a mixture thereof. Some or all of the memory 208 can be portable, such as a disk, card, memory stick, cartridge, and the like.

The processor 206 can include appropriate signal conditioners to transmit and receive desired information (e.g., data), and correspondingly may include filters, amplifiers, limiters, modulators, demodulators, CODECs, signal format converters (such as analog-to-digital and digital-to-analog converters), clamps, power supplies, power converters, and the like, as needed to perform various control, communication, evaluation, and processing operations described herein. The processor 206 can be comprised of one or more components of any type suitable to process input signals and provide desired output signals. Such components may include digital circuitry, analog circuitry, or a combination of both. The processor 206 can be of a programmable type; a dedicated, hard-wired state machine; or a combination of these; and can further include multiple processors, arithmetic-logic units (ALUs), central processing units (CPUs), or the like. For forms or the processor 206 with multiple processing units, distributed, pipelined, and/or parallel processing can be utilized.

As described above, the processor 206 includes one or more modules that examine the sensory data obtained by the sensor 108 (shown in FIG. 1) of the device 104 to determine relevant data. The processor 206 can include one or more modules that analyze the relevant data to identify surrogate biomarker, also as described above. The algorithms 224, 228 (shown in FIG. 2) that determine the relevant data 222 and/or the surrogate biomarker 226 may be represented by one or more of the modules. The modules may be formed based on one or more sets of instructions stored on the memory 208. Alternatively, one or more of the modules may be an additional processor.

In the illustrated embodiment, the modules include an input/output (I/O) module 210. The I/O module 210 receives the sensory data transmitted from the device 104 to the transceiver 204 and conveys the sensory data to one or more other modules. The I/O module 210 may communicate relevant data and/or surrogate biomarker derived from the sensory data by one or more of the modules to the transceiver 204 for communicating the relevant data and/or surrogate biomarker to the device 104 and/or one or more of the computing devices 200, 202, 218, 220.

The modules can include an authentication module 212 that identifies the patient who is carrying the device 104 based on the sensory data. For example, the authentication module 212 can receive at least some of the sensory data collected by the device 104 that represents motion of the device 104. The authentication module 212 determines whether the person who is carrying the device 104 (and whose movements are reflected by the sensory data) is the patient associated with the device 104. In one embodiment, the authentication module 212 creates an individual and/or unique movement signature for a patient based on collected baseline movement data. The baseline movement data may be a set of the sensory data that is collected over a period of time, such as a minute, an hour, a day, a week, or a month and that is stored in the memory 208. For example, sensory data such as the sensory data 300, 302, 304 shown in FIG. 4 can be collected as baseline movement data and stored in the memory 208. The baseline movement data can be stored in the memory 208 in a database, list, table, or other memory structure that associates the baseline movement data, or one or more features of the baseline movement data, with the patient.

The authentication module 212 generates the movement signature of a patient by extracting features of interest from the baseline movement data. For example, the sensory data 300, 302, 304 shown in FIG. 4 can be used as baseline movement data. The sensory data 300, 302, 304 can represent an average, median, or other statistical measure of several sets of baseline movement data acquired at different times for the patient. Alternatively, the sensory data 300, 302, 304 can include data that is not averaged or otherwise combined with movement data acquired at another time.

The authentication module 212 may determine relevant data as one or more features of interest of the baseline movement data. For example, the authentication module 212 can calculate an average, median, or other statistical measure of a tremor in a selected frequency range and/or temporal range of the baseline movement data. As another example, the authentication module 212 can calculate an average, median, or other statistical measure of a magnitude of the baseline movement data, a number, average, or median count of a particular good or poor behavior, an average or median activity level, a measured amount of sway, an average, median, or other statistical measure of a magnitude, frequency, and/or duration of movement by the patient along one or more axes after the patient stumbles, and/or one or more other measures or portions of the baseline movement data that may otherwise be evaluated non-quantitatively in clinical practice and that relates to movement.

As additional examples, the authentication module 212 may identify several waveform segments in the movement data 300, 302, 304 as features of interest. The waveform segments can include peak waveform segments 310, 312, 314, 316, 322, 324, 326 and valley waveform segments 318, 320. The peak waveform segments 310, 312, 314, 316, 322, 324, 326 include portions of the movement data having larger amplitudes or accelerations than one or more other portions of the same movement data. The valley waveform segments 318, 320 include portions of the movement data having smaller amplitudes or accelerations than one or more other portions of the same movement data. The peak waveform segments and valley waveform segments may be identified by comparing the sensory data 300, 302, 304 to one or more thresholds and identifying the peak waveform segments when the sensory data 300, 302, 304 exceeds a corresponding threshold and identifying the valley waveform segments when the sensory data 300, 302, 304 drops below a corresponding threshold. Alternatively, one or more of the peak waveform segments or valley waveform segments can be identified by transforming the time-domain baseline movement data into a frequency-domain representation of the baseline movement data (e.g., via a Fourier transform). One or more features of interest may be identified based on the frequencies at which various waveform segments (e.g., peak waveform segments and/or valley waveform segments) appear in the frequency-domain representation of the baseline movement data.

In one embodiment, the features of interest of baseline movement data can include the relative times at which the waveform segments appear in the baseline movement data. For example, the authentication module 212 can determine that the peak waveform segment 310 occurs at a first time $t_1$, the valley waveform segment 318 occurs at a second time $t_2$, the peak waveform segment 324 occurs at a third time $t_3$, the valley waveform segment 320 occurs at a fourth time $t_4$, the peak waveform segment 312 occurs at a fifth time $t_5$, the peak waveform segment 314 occurs at a sixth time $t_6$, the peak waveform segment 326 occurs at a seventh time t7, and the peak waveform segment 316 occurs at an eighth time t8. One or more features of interest of the baseline movement data can include the differences in time between the waveform segments. For example, a first feature of interest can include the valley waveform segment 320 occurring before the peak waveform segment 312 by the time difference between the fourth and fifth times $t_4$, $t_5$. A second feature of interest can include the peak waveform segments 312, 314 sequentially occurring at times separated by the difference between the fifth and sixth times $t_5$, $t_6$. Other features of interest can be derived by the authentication module 212. The above are merely provided as examples.

The features of interest that represent relevant data can include the time periods over which one or more waveform segments occur. For example, the time period that extends between when a peak waveform segment exceeds a threshold and when the peak waveform falls below the threshold may be a feature of interest. In another example, the features of interest can include shapes of the waveform segments. The shapes of the waveform segments can be determined by comparing a waveform segment to one or more waveform templates (e.g., predetermined shapes such as wavelets). The areas encompassed by the waveform segment (e.g., the integrated area between the waveform segment and a baseline or a threshold) and the waveform template can be compared. The slope or other aspects of the waveform segments can be compared to the waveform templates. The differences between the areas, slopes, and the like of the waveform segments and the waveform templates can be used to identify the shapes of the waveform segments. The features of interest and/or the movement signatures may be stored in the memory 208.

In one embodiment, the authentication module 212 uses the features of interest in the baseline movement data to create the movement signature for the patient. The movement signature may be unique to the patient (e.g., no other patient having movement data stored on the memory 208 has an identical movement signature) and/or may be individual to the patient (e.g., one or more other patients have the same or similar movement signatures, but at least 99%, 98%, 95%, 90%, or some other threshold of the patients have different movement signatures). The movement signature for a patient may be defined as a pattern of features of interest. A pattern can include a plurality of features of interest that occur at times that are relative to each. For example, a pattern may indicate when a first feature of interest occurs, when a second feature of interest occurs relative to the first feature of interest, when a third feature of interest occurs relative to the first and second features of interest, and so on. A pattern may include when one or more waveform segments occur relative to each other (e.g., the time difference between when the waveform segments occur), one or more clusters of features of interest occurring within a time window, and the like. Other correlations between features of interest and the times at which the features of interest occur in the baseline movement data may be used as a pattern.

The authentication module 212 can compare sensory data acquired by the device 104 (shown in FIG. 1) with the movement signatures of a plurality of patients to determine if the sensory data represents a specific patient. For example, the authentication module 212 can receive recently acquired sensory data and extract features of interest from the sensory data, as described above. The features of interest from this sensory data can be compared to the features of interest in each of the plurality of movement signatures. The amount or degree of match between the features of interest in the sensory data and the features of interest in the movement signatures can be used to determine if the sensory data represents movements of a specific patient associated with a particular movement signature. For example, if at least a threshold percentage of the features of interest in the sensory data also are in the movement signature, then the sensory data may be authenticated as being representative of movements of the same patient that is associated with the movement signature. On the other hand, if less than the threshold percentage of the features of interest in the sensory data is in the movement signature of a patient, then the sensory data may not be authenticated as being representative of movements of the patient. The identity of the patient that is determined based on the comparison of the sensory data with the movement signatures can be one type of relevant data, as described above.

In one embodiment, the authentication module 212 examines different sets of baseline movement data of a patient to generate location signatures that are associated with the patient. A location signature can be used by the authentication module 212 to determine where the device 104 is carried by the patient. The authentication module 212 can obtain sensory data from the device 104 that represents motions of the patient or from the memory 208, determine features of interest of the sensory data, compare the features of interest of the sensory data to features of interest of one or more location signatures associated with different locations on or around the patient, and determine where the device 104 is carried by the patient by an amount or degree of match between the features of interest of the sensory data and the features of interests of the location signatures. For example, the authentication module 212 can determine if the device 104 is carried in the back-right pants pocket, the back-left pants pocket, the front-right pants pocket, the front-left pants pocket, the right or left shirt pocket, one or more pockets in a jacket or coat worn by the patient, and the like. The location of the device 104 can be another type of relevant data.

In order to generate the location signatures, the device 104 can provide a location that the device 104 is located on the patient along with the sensory data (e.g., the sensory data 300, 302, 304 shown in FIG. 4) that is collected when the device 104 is in the location. This sensory data may be used as baseline movement data. The patient may provide the location of the device 104 as input to the device 104, and the device 104 may transmit the location to the authentication module 212. The authentication module 212 associates the baseline movement data with the location of the device 104 when the baseline movement data is acquired. The baseline movement data that is acquired at different time periods but from the same location on the patient may be identified by the authentication module 208 as a set of baseline movement data. Several different sets of baseline movement data can be acquired, with each set including movement data that is acquired when the device 104 is carried by the patient in a different location. Features of interest can be extracted from the baseline movement data of each set, and the features of interest may be used to form location signatures associated with the different sets, similar to as described above. Each location signature can correspond to a different location that the patient carries the device 104.

The authentication module 212 can compare the features of interest of the sensory data with features of interest of one or more location signatures associated with the patient. If the features of interest in the sensory data match the features of interest in a location signature (e.g., at least a predetermined threshold percentage of the features of interest of the sensory data and the features of interest in the location signature are the same or within a predetermined threshold of each other), then the location that is associated with the location signature can be identified as the location used by the patient to carry the device 104. On the other hand, if the features of interest in the sensory data do not match the features of interest in a location signature (e.g., less than the predetermined threshold percentage of the features of interest are the same), then the location that is associated with the location signature is not identified as the location used by the patient to carry the device 104.

Returning to the discussion of the modules of the processor 206, the modules can include a processing module 214 that determines the relevant data from the sensory data received from the device 104. For example, the processing module 214 can be implemented in one or more of the algorithms 224 (shown in FIG. 2) that derive the relevant data 222 (shown in FIG. 2) from the sensory data 220 (shown in FIG. 2). The processing module 214 can determine the relevant data in one or more manners similar to the authentication module 212 described above. For example, the processing module 214 can calculate one or more of the features of interest that are described above from the sensory data received from the device 104. As described herein, the features of interest can be used to determine surrogate biomarkers of the patient.

The processor 206 includes an analysis module 216 that examines the relevant data to determine surrogate biomarkers. The analysis module 216 may be implemented as one or more of the algorithms 228 (shown in FIG. 2) that identify the surrogate biomarker 226 (shown in FIG. 2) from the relevant data 222 (shown in FIG. 2). As described above, the surrogate biomarker can include deviation of the relevant data for the patient from an average, median, or other statistical measure of the relevant data of a sample of other patients and/or healthy persons, acceleration levels based on activity types, autocorrelation functions, Fourier components and/or wavelets of the motion represented by the relevant data, percentiles or other fractions of activity levels, and/or other features of the relevant data.

In one embodiment, the analysis module 216 examines the relevant data to determine one or more patterns of the relevant data. As described above, a pattern may include a set of a plurality of features of interest in the relevant data that occur at times relative to each other. The analysis module 216 may derive patterns of the relevant data to identify activities and/or activity transitions of the patient who is carrying the device 104. The identified activities and/or activity transitions can be surrogate biomarkers.

For example, the analysis module 216 can derive patters of the relevant data and determine which activities the patient engaged in (e.g., walking, sitting, lying down, or riding in a wheelchair) and/or transitions between activities of the patient (e.g., starting to walk after standing still, standing still after walking, sitting from a standing position, or standing from a sitting position). In one embodiment, the analysis module 216 determines the activities and/or transitions between activities of a patient by determining a posture of the patient and/or changes in the posture from patterns in the relevant data associated with the patient. As used herein, the term "posture" refers to the spatial configuration of a patient's body, and may include the position (or change in position) of one portion (e.g., appendages) of the body relative to another portion. The identification of activities and/or activity transitions of the patient can be achieved by monitoring changes in the posture of the patient. For example, a sequence of posture determinations that are derived over time can provide information about the movements, activities, and activity transitions of the patient.

In one embodiment, the analysis module 216 determines different postures of the patient based on patterns of vibrations in the biomechanical system of the patient. These vibrations may be the result of large movements of the patient (e.g., walking) and/or the result of smaller tremors (e.g., tremors that are perceivable by the human eye and/or tremors that are not perceivable by the human eye). Vibrations can be characterized as changes in velocity of movements of the patient, which is a form of acceleration. Because acceleration corresponds to the second derivative of position with respect to time, integration of the sensory data obtained by the sensor 108 over time may be applied to calculate velocity of one or more body parts or appendages of the patient. The calculated velocity may be relevant data calculated from the sensory data.

With respect to the sensory data shown in FIG. 4, integrating one or more waveform segments in the sensory data 300, 302, and/or 304 over time can provide velocity calculations. The velocity calculations represent movement of the sensor 108 and, correspondingly, of the patient. The velocity calculations can be integrated over time to provide position data as relevant data of the patient. The position data can represent one or more positions of the patient and/or of appendages of the patient.

Alternatively, another, different technique for calculating position or posture information from the sensory data may be used. For example, the measured vibrations represented by the sensory data can be analyzed that determine an estimated position of one or more portions of the patient's body. As described above, machine learning algorithms may be used to determine such positions.

In one embodiment, posture of the patient can be determined by measuring one or more apparent imperfections in the muscular system of the patient that are represented by patterns of vibrations or tremors of the patient. Even at rest in a healthy person, the body of the person may be in motion in the form of relatively small vibratory motions referred to as tremors. These slight, often imperceptible movements can be caused by a number of factors including respiratory motion, the carbioballistic impulse, fluctuating muscle activation during postural resistance to gravity, resonant motion due to joint stiffness, and the like. The combination of these factors can lead to vibrations at relatively fast timescales (e.g., in the frequency range of 1 to 25 hertz). The vibrations may vary in characteristic or signature ways that are dependent upon the posture of the patient.

The type of tremor can depend on the joint or joints of the patient that are causing the motion. A joint may have a natural resonant frequency that the joint vibrates. The resonant frequency can be caused by stabilizing perturbations of an appendage joined to the joint. As the moment of inertia increases in the patient (e.g., by increasing the mass and/or size of the appendage joined to the joint), the resonant frequency at which the joint vibrates may decrease. For example, the resonant frequencies for fingers may be 25 hertz, 6 to 8 hertz for the wrist, 3 to 4 hertz for the elbow, and 0.5 to 2 hertz for the shoulder joint. Alternatively, different resonant frequencies may apply to one or more of these joints. The resonant frequency of a joint can be modulated by muscle stiffness. For example, stiffer muscles joined to or interconnected with a joint can cause increases in the resonant frequency of the joint relative to patients having less stiff muscles.

As for one example of determining a posture of the patient, the posture of the forearm of the patient can be determined through detected patterns of the small, vibratory movements of the hand that is holding the device 104. The small, vibratory movements can be measured as sensory data by the device 104. The direction of these movements can be used to determine the orientation of the forearm and/or whether or not the arm is stabilized (e.g., with the elbow of the patient disposed on or off a surface such as a table). As indicated above, the description herein provides a technique in which measured vibrations can be used to determine or estimate the actual position of one or more portions of the body of the patient. While other approaches for developing this technique are contemplated and fall within the scope of the present application, the following approach is provided as one example. It should be appreciated that the following approach is only one example, and that modifications and variations to the same are contemplated. For example, one or more machine learning algorithms may be employed. Further, the following approach is provided for illustration purposes only, and not all embodiments of the subject application should be limited to such approach. For example, while the description below includes a patient holding the device 104 in his or her hand and the posture of the arm of the patient is identified by the analysis module 216 based on patterns in the tremors derived from the sensory data collected by the device 104, alternatively, the device 104 may be disposed in a pant pocket, shirt pocket, a belt holster, and the like to identify the posture of the patient.

The patient may hold the device 104 in his or her hand while the device 104 obtains sensory data, such as the sensory data 300, 302, 304 shown in FIG. 4. The processing module 214 receives sensory data from the device 104 and can calculate estimates of the azimuth and orientation of the forearm of the patient that is holding the device 104 as relevant data. In one embodiment, the processing module 214 uses a minimum variance analysis technique to determine the azimuth and orientation. For example, acceleration vectors (e.g., magnitude and direction) can be determined as relevant data that is derived from the sensory data. As described above with respect to the sensory data 300, 302, 304, the magnitude of the sensory data can be represented by the vertical height of the movement data along the vertical axis 308. The direction of the sensory data can be determined based on which axis of movement is represented by each of the sensory data 300, 302, 304. For example, each of the sensory data 300, 302, 304 can represent movement along a different axis.

One or more covariance matrices may be formed from acceleration vectors that are calculated by the processing module 214 from the sensory data. For example, 3×3 covariance matrices of the acceleration vectors may be formed and factored by eigenvalue decomposition. In one embodiment, the axis of relatively small movements may be along the direction of the eigenvector that corresponds to an eigenvalue that is smaller than one or more other eigenvalues. The azimuth and inclination angle (e.g., orientation) of the forearm of the patient can be estimated from this direction of the eigenvector using the following relationships:

$$j = \arcsin\left(\frac{z}{\sqrt{x^2 + y^2}}\right) \quad \text{(Equation \#1)}$$

$$a = \arcsin\left(\frac{x}{\sqrt{x^2 + y^2}}\right) \quad \text{(Equation \#2)}$$

where φ represents the azimuth of the forearm, a represents the inclination angle (or orientation) of the forearm, arc sin(f) represents the arcsine function, x represents an amount of movement (e.g., distance) by the device 104 along a first direction, y represents an amount of movement (e.g., distance) of the device along a second direction that is orthogonal to the first direction, and z represents an amount of movement (e.g., distance) by the device 104 along a third direction that is orthogonal to the first and second directions. In one embodiment, a correction may be applied to the azimuth (φ) and/or the inclination angle (α) to more closely correlate the calculated azimuth (φ) and/or inclination angle (α) with previously determined azimuth (φ) and/or inclination angles (α).

The calculated azimuth (φ) and/or inclination angle (α) of the forearm represent a calculated posture of the forearm of the patient. A similar technique can be used to calculate postures of other body parts of the patient, such as hips, legs, fingers, and the like. The posture of a body part of the patient can have a characteristic effect on a pattern of micromovements that are sensed by the sensor 108 (shown in FIG. 1). For example, for a given body part (e.g., arm, leg, fingers), the body part may be associated with a pattern (e.g., one or more features of interest in the sensory data occurring at corresponding relative times) of movements that are sensed by the sensor 108. As another example, a spatial pattern of tremors may be associated with a posture of a body part or the patient. This pattern may change based on a change in the azimuth (φ) and/or inclination angle (α) of the body part. For example, one or more waveform segments and/or the relative times at which the waveform segments occur for the same body part may change for different postures of the body part.

Figure 7:
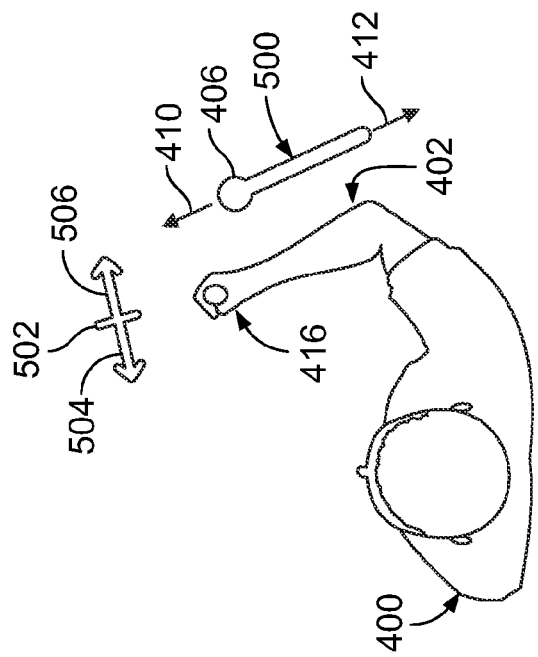
FIGS. 6 and 7 are schematic diagrams of an example patient.
Figure 6:
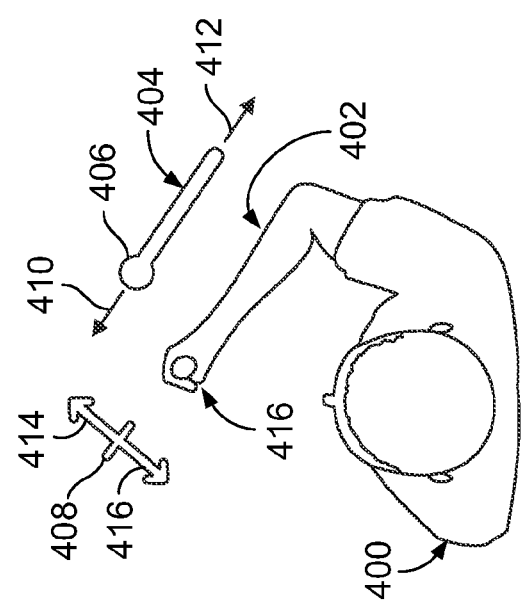

FIGS. 6 and 7 are schematic diagrams of an example patient 400 with a forearm 402 in different positions. Azimuthal markers 404, 500 are shown to represent the different azimuths (φ) of the forearm 402 in the different positions, with circles 406 on the azimuthal markers 404, 500 representing the location of the device 104 (shown in FIG. 1) in a hand 416 of the patient 400. The azimuthal markers 404, 500 and forearm 402 are oriented along, or parallel to, opposite directions referred to herein as a front direction 410 and a back direction 412. Lateral markers 408, 502 are shown to represent opposite lateral directions 414, 416 and 504, 506 that are oriented perpendicular to the azimuthal markers 404, 500.

FIGS. 8 through 10 are examples of displacement data 600, 700, 800. The displacement data may represent relevant data that is calculated from the sensory data obtained by the device 104 (shown in FIG. 1) being held in the hand 416 (shown in FIG. 6) of the patient 400 (shown in FIG. 6). The displacement data 600, 700, 800 represents movements of the device 104 when the elbow of the patient 400 is on a surface, such as a table. For example, the displacement data 600, 700, 800 may represent tremors or other vibrations of the device 104. The displacement data 600 represents movements obtained when the forearm 402 (shown in FIG. 6) is oriented at an inclination angle (α) of 14 degrees and at azimuth (φ) of −26 degrees. The displacement data 700 represents movements obtained when the forearm 402 is oriented at an inclination angle (α) of 9.3 degrees and at azimuth (φ) of −4.5 degrees. The displacement data 800 represents movements obtained when the forearm 402 (shown in FIG. 6) is oriented at an inclination angle (α) of 14 degrees and at azimuth (φ) of −26 degrees. The displacement data 600, 700, 800 are shown alongside horizontal axes 602, 702, 802 representative of movement or displacements of the device 104 along one or more of the lateral directions 414, 416 (shown in FIG. 6) or 504, 506 (shown in FIG. 7) and alongside vertical axes 604, 704, 804 representative of movement or displacements of the device 104 along the front direction 410 and the back direction 412 (shown in FIG. 6).

The displacement data 600, 700, 800 is shown as individual markers 606, 706, 806 that indicate different vibrations of the device 104 (shown in FIG. 1). As shown in each of FIGS. 7 through 9, the markers 606, 706, 806 are generally arranged in spatial patterns 608, 708, 808. The spatial orientation of the patterns 608, 708, 808 corresponds to the orientation of the forearm 402 of the patient 400 (shown in FIG. 6). For example, the forearm 402 of the patient 400 is generally oriented perpendicular to the directions in which each of the patterns 608, 708, 808 is elongated, as shown by the azimuthal markers 610, 710, 810 shown in FIGS. 8 through 10.

While the example embodiment shown in FIGS. 8 through 10 focuses on determining the posture of a forearm while an elbow of the patient is on a surface, the technique may be applied to identify postures of other body parts. For example, the sensory data may be collected when the device 104 (shown in FIG. 1) is in a back pants pocket of the patient and can indicate tremors of the patient, whether the patient is walking (e.g., by the accelerations measured along a plurality of the axes), whether the patient is upright or laying down, and the like.

Returning to the discussion of the system 100 shown in FIG. 5, the analysis module 216 can determine an activity of the patient based on the postures of the patient. For example, the analysis module 216 can estimate a posture of the patient (e.g., standing, sitting, or lying down) as described above and identify a movement activity of the patient based on the posture. In one embodiment, different activities can be associated with different postures and different relevant data. For example, walking can be associated with an upright posture of the patient and relevant data representative of relatively small vertical displacements (e.g., the up and down movements associated with walking) that do not exceed one or more first thresholds. As another example, running can be associated with an upright posture of the patient and relevant data representative of relatively large vertical displacements that exceed one or more second thresholds that are larger than the first thresholds. In one embodiment, sitting can be associated with an upright posture and relevant data representative of small vertical displacements and/or relatively small displacements in other directions. Other activities can be identified in similar manners.

Figure 11:
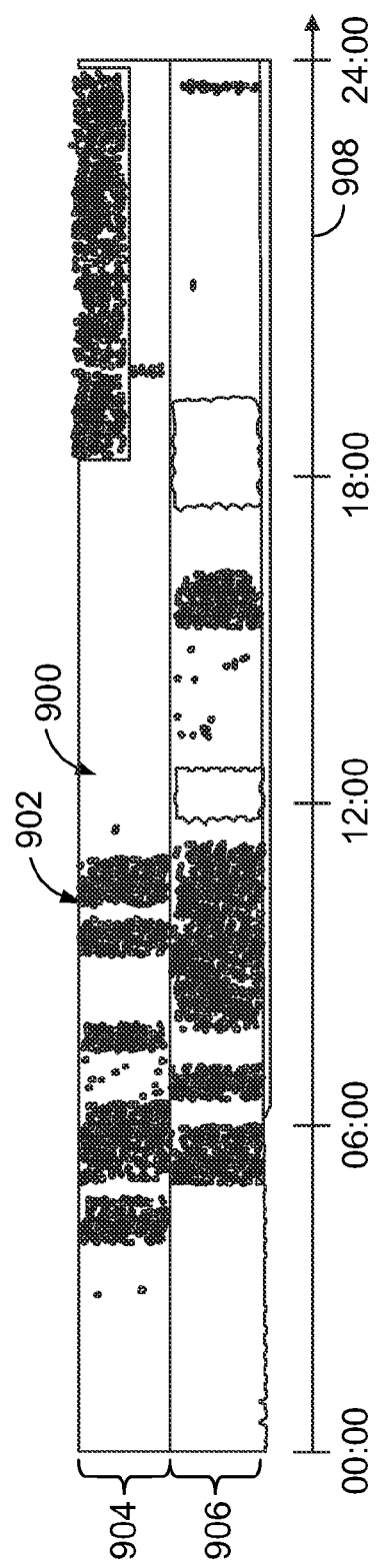
FIG. 11 is a graphical representation of examples of relevant data derived by a processing module of the system shown in FIG. 5.

FIG. 11 is a graphical representation of activities identified by the analysis module 216 in accordance with one example. The analysis module 216 can track the times at which the patient engages in different activities 900, 902. In the illustrated example, the activities 900 represent time periods when the patient is sitting, standing, or lying down (e.g., not walking) and the activities 902 represent time periods when the patient is walking (e.g., not sitting, standing still, or lying down). While only two activities 900, 902 are shown in FIG. 11, additional activities may be shown. The activities 900, 902 are arranged into two horizontal rows 904, 906 along a horizontal axis 908. The horizontal axis 908 represents time, such as the hours of a day and each row 904, 906 represents a different day.

As shown in FIG. 11, several periods 910 of the activity 902 are separated from each other by several periods 912 of the activity 900. For example, the patient may have walked during the periods 910 and paused to rest during the periods 912. The times at which the patient changed activities 900, 902, such as the times at which a period 910 ends and a period 912 begins, or a period 912 ends and a period 910 begins, can be identified by the processing module 214 (shown in FIG. 5) as an activity transition.

The analysis module 216 may generate surrogate biomarkers based on patterns of the activities and/or activity transitions. For example, the frequency at which the periods 910 occur, the time duration of the periods 910 and/or 912, the number of the periods 910 and/or 912, and the like, may be surrogate biomarker. The surrogate biomarker can include a trend in the relevant data, such as a pattern of periods 910, 912 of different types of activities 900, 902, such as the types of activities, the times at which the activities are performed, the duration of activities, and the like. In one embodiment, a trend may include a type of mixture of activities 900, 902, such as a combination or sequential order and/or frequency of different activities 900, 902 that occur over a day, week, month, year, and the like. As another example, a trend in activities can represent characteristics of the movements associated with the movement data. For example, a trend may be a gradual change in a gait of the patient when the patient is walking that is identified over several days, weeks, months, or years. As another example, a trend may include a gradual change in tremors of the patient, such as a change in amplitude, direction, and/or frequency of sensory data acquired by the sensor 108 (shown in FIG. 1) and associated with tremors over days, weeks, months, years, and the like.

The analysis module 216 can determine surrogate biomarker from the relevant data in order to provide a knowledge base for a physician giving medical care to the patient. This knowledge base can include information about how the patient performs various activities (e.g., walking, standing, sitting, and the like) during everyday life. The surrogate biomarker can provide the physician with knowledge of how symmetrical the activities of the patient are. The surrogate biomarker can be used by the physician as insight into causes for various impairments of the patient.

In one embodiment, the analysis module 216 employs machine learning to provide clinical diagnostics concerning the patient as the surrogate biomarker. The clinical diagnostics can include a detection of whether the patient suffers from one or more different diseases or impairments and/or an extent (e.g., disease state) to which the patient suffers from the disease or impairment. For example, the analysis module 216 can provide, as surrogate biomarker, a potential diagnosis of Parkinson's disease, spinal cord injury, multiple sclerosis, cerebral palsy, cerebellar ataxia, and the like. The analysis module 216 may determine surrogate biomarker that represents changes in a severity of the disease or impairment and recommended changes in medication or drug dosage on a periodic basis, such as a daily basis, based on the movements represented by the relevant data. In one embodiment, the analysis module 216 may provide an estimated condition of the patient based on the relevant data as the surrogate biomarker. Such an estimated condition may include, but is not limited to, the age, strength, or agility of the patient. As described above, machine learning algorithms can be used to provide the surrogate biomarker. For example, the relevant data of a patient may be compared to the relevant data of a sample of persons having known surrogate biomarker associated with the persons. Similarities and/or differences between the relevant data between the patient and the persons of the sample may be used to derive surrogate biomarker about the patient from the known surrogate biomarker of the persons in the sample.

In one embodiment, at least some of the sensory data may be acquired outside of a clinical environment by the device 104 in order to mimic or replicate a clinical examination. For example, a physician may perform a timed up and go (TUG) examination on the patient to assess a progression or state of Parkinson's disease. The test can be a timed test that examines the time period required for a patient stand up from a sitting position, walk a predetermined number of paces from chair, return to chair, and sit back down. In the daily life of the patient, the patient may stand up from a sitting position and walk a number of strides. These movements can be used to perform surrogate TUG examinations outside of the clinical environment. For example, the device 104 can obtain sensory data when the patient stands up from a sitting position and walks during the daily life of the patient. The evaluation station 102 can receive the sensory data, identify an activity transition from sitting to standing, count the number of strides of the patient, and measure that time, as would be naturally a part of person's normal daily activities. The time involved in performing the activity transition and the walking can be used as an estimate of the TUG examination. As the patient may stand up and walk several times a day, the system 100 can estimate the TUG examination multiple times per day.

As another example of surrogate biomarkers that may be derived by the evaluation station 102, the evaluation station 102 may identify a frequency or number of times that gait lock occurs during a time period. Gait lock can be a symptom of Parkinson's disease and other neurodegenerative disorders where the patient's gait is frozen and stops. The number of times that gait lock occurs may be determined by the evaluation station 102 by identifying activities and/or activity transitions of the patient. The evaluation station 102 may develop a metric of the gait lock as a surrogate biomarker. The metric can include a percentage of strides where gait lock was detected, a duration of gait lock, an amplitude of tremors during the gait lock, and the like. In one embodiment, such a surrogate biomarker can be combined with other surrogate biomarkers (e.g., an identification of a standing activity of the patient) to identify a trend toward falling, a risk of falling, and/or a warning of an impending fall.

The analysis module 216 can provide the surrogate biomarker to the patient and/or the physician through the network 106. For example, the analysis module 216 can cause a signal to be formed by the processor 206 and transmitted to the physician CPU 200 and/or the device 104 of the patient through the Internet and/or one or more other networks. The signal can cause the physician CPU 200 to output the surrogate biomarker in a manner that enables the physician to comprehend the surrogate biomarker and modify the therapy provided to the patient. For example, the physician CPU 200 can visually present (e.g., display on a computer monitor or print on paper) text and/or images that describe the surrogate biomarker.

In another example, the analysis module 216 can report the surrogate biomarker to the insurance CPU 202. The insurance CPU 202 can receive the surrogate biomarker and use the information in conjunction with determining financial insurance benefits of the patient. For example, the insurance CPU 202 may provide the patient with a discount or decreased premium when the activities of the patient (as represented by the surrogate biomarker and/or relevant data) conforms to an exercise schedule and such conformance is proven by the surrogate biomarker and/or relevant data.

In one embodiment, the evaluation station 102 and/or the device 104 may examine the sensory data acquired by the sensor 108 (shown in FIG. 1) to provide a real time intervention to the patient. A real time intervention includes a notification provided by the analysis module 216 to the device 104 and/or by the device 104 alone to the patient based on relevant data. For example, the device 104 may include one or more modules similar to the processing module 214 and/or the analysis module 216 of the evaluation station 102. The modules in the evaluation station 102 and/or the device 104 may provide cues to the patient when certain relevant data is identified.

For example, and as described above, the evaluation station 102 and/or the device 104 can provide real time and/or clinical interventions either directly to the patient (in the case of real time interventions) or indirectly through the healthcare provider of the patient. The real time intervention can be generated based on detected changes in activities of the patient to trigger cueing to the patient via the device 104. The real time intervention can direct the patient to change an activity (e.g., gait or posture) as reinforcement to a clinical training of the patient. The cueing can involve sending a notification to the device 104 in real time, or in a relatively short time period following detection of an activity (e.g., within a few seconds or minutes). The clinical intervention can be provided to a healthcare provider, such as a physician, and/or the patient when values of one or more surrogate biomarkers (such as posture and/or gait) approach clinically established danger levels or thresholds. The clinical intervention can include a fall prevention alarm that is sent to the device 104 and/or that is generated by the device 104 and that suggests that the patient cease the current activity, contact a third party for assistance, and the like.

Other examples of interventions that may be generated by the device 104 and/or by the evaluation station 102 and sent to the device 104 are notifications to the patient to perform activities when no activities are identified by the device 104 based on the relevant data and/or when one or more activities (or a lack thereof) are identified. For example, the device 104 may compare current activities of the patient based on the relevant data with an exercise schedule to determine if the patient is performing the exercises of the schedule. If the patient is not performing the exercises, the device 104 may prompt the patient to do so with one or more visual, audible, and/or tactile alarms (e.g., a flashing light or display, an audible alarm, and/or vibrations of the device 104).

In another example, the device 104 may monitor the relevant data to determine if the detected motion of the patient indicates that the patient may be leaning too far to one side and is at risk of falling. For example, the device 104 can compare the measured accelerations of the sensory data to one or more thresholds. If the measured accelerations exceed the threshold, then the device 104 may determine that the patient is at increased risk of falling and can provide one or more visual, audible, and/or tactile alarms to warn the patient and potentially prevent the patient from falling.

In another example, the device 104 may periodically remind the patient when to take prescribed medication. For example, the device 104 can notify the patient on a periodic basis according to a medication schedule as to when the next dosage of medication should be taken. Alternatively, the device 104 may direct the patient to take prescribed medications when indicated by features of the obtained data, such as one or more surrogate biomarkers.

As another example, the device 104 and/or the evaluation station 102 may transmit an alarm to one or more of the computing devices 200, 202, 218, 220 to warn the respective computing devices 200, 202, 218, 220 of an alarm state. An alarm state may exist when one or more surrogate biomarkers exceed one or more predetermined limits. For example, when motion of the patient stops (e.g., gait lock) for at least a predetermined time, when the patient has fallen or is about to fall, and the like, the device 104 and/or evaluation station 102 can transmit a signal to one or more of the computing devices 200, 202, 218, 220 to warn users of the computing devices 200, 202, 218, 220 of the alarm state. With respect to the physician CPU 200 and/or the emergency personnel CPU 218, the alarm may cause responders to be directed to a location of the patient that is determined based on the GPS sensor 128 in the device 104. For example, the alarm may direct an ambulance to be sent to the patient. With respect to the family/friend CPU 220, the alarm may notify the computing devices of one or more predesignated family members and/or friends of the alarm state.

Figure 12:
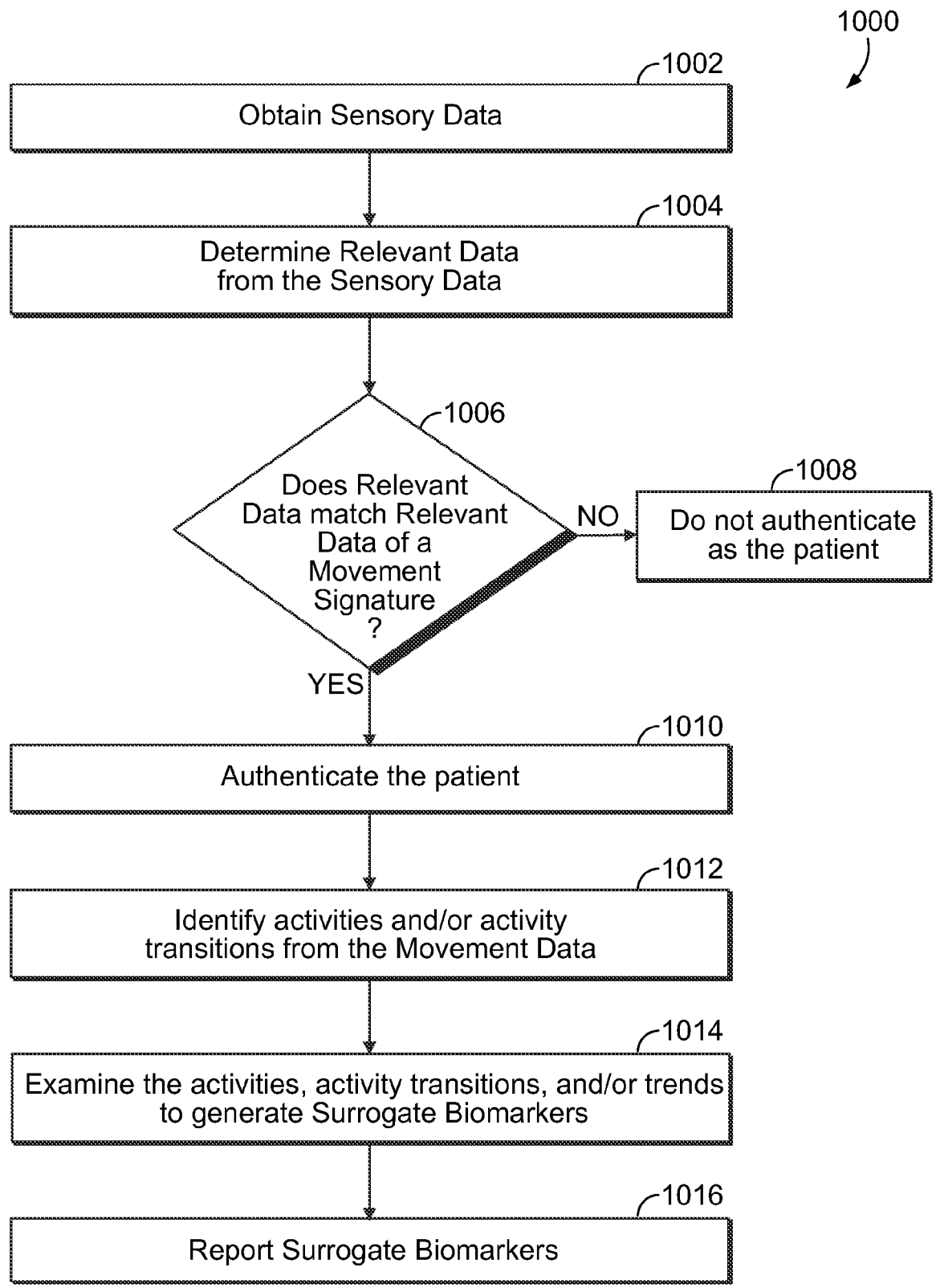
FIG. 12 is a flowchart of one embodiment of a method for evaluating sensory data acquired by a sensor of a mobile device to determine medically relevant data and/or surrogate biomarker.

FIG. 12 is a flowchart of one embodiment of a method 1000 for evaluating sensory data acquired by a sensor of a mobile device to determine medically relevant data and/or surrogate biomarker. The method 1000 may be used in conjunction with one or more embodiments described above. For example, the method 1000 may be used to obtain sensory data of a patient in a continuous or near-continuous manner (e.g., at a sampling frequency of 10 hertz) for a substantial portion of the day (e.g., when the patient has the device 104 in his or her possession) using a hand held or otherwise portable device, such as a mobile phone. As described above, the sensory data is examined to determine relevant data and/or surrogate biomarker.

At 1002, sensory data of the patient is obtained. As described above, the sensory data can be obtained by an accelerometer and/or gyroscope disposed in a mobile phone.

At 1004, the sensory data is examined to determine relevant data of the patient. As described above, one or more features of interest of the sensory data may be identified as the relevant data.

At 1006, the relevant data based on sensory data of a patient may be examined to authenticate the patient. For example, one or more features of interest of the sensory data may be identified as relevant data and compared to one or more features of interest of movement signatures associated with different patients. If at least a predetermined percentage or fraction of the features of interest of the sensory data are not the same as or similar to the features of interest of a movement signature, then the relevant data may indicate that the patient from whom the sensory data is acquired is not the patient associated with the movement signature. As a result, flow of the method 1000 continues to 1008. On the other hand, if at least the threshold percentage of the features of interest of the sensory data are the same or similar to the features of interest of the movement signature, then the relevant data may indicate that the patient is the same patient with whom the movement signature is associated. As a result, flow of the method 1000 continues to 1010.

At 1008, the person from whom the sensory data was obtained is not authenticated as the patient. For example, the person carrying the device 104 that obtained the sensory data may not have generated sensory data that corresponds with the movement signature of the patient. Therefore, the sensory data is unlikely to be from the patient and the person is not authenticated as the patient.

At 1010, the person from whom the sensory data was obtained is authenticated as the patient. For example, the person carrying the device 104 that obtained the sensory data may be the patient and the sensory data is likely to be generated by the patient.

At 1012, relevant data is derived from the sensory data. As described above, the relevant data can include identifications of activities performed by the patient, activity transitions of the patient, and the like. The relevant data may be derived from the sensory data using machine learning algorithms.

At 1014, the relevant data is analyzed to generate surrogate biomarker about the patient. As described above, the surrogate biomarker may include summaries of the percentage, ratio, or other fractions of time that the patient is active and/or sedentary; a quantitative measure of accelerations of the patient; a quantitative measure of movement cycles of the patient; classifications of the relevant data; regressions of the relevant data; trending of the relevant data; identifications from the relevant data; magnitudes and/or durations of tremors of the patient; positive or negative progressions in the disease state of the patient; impacts of medication on the disease state of the patient; trends in the biomarkers; and the like. The surrogate biomarkers may be recorded into a report that is communicated to the patient, one or more healthcare providers (such as a primary care physician and/or one or more other physicians), insurance companies, and the like. The report may include a variety of information concerning the patient, including activity recognitions, biomarkers, trends in the biomarkers, estimated quantitative scores or measures for a clinical rating system, estimates for examinations typically performed in a clinical environment, and the like. The reports can be tailored or customized based on the recipient of the report. For example, different recipients of the reports can receive different information in the received reports.

At 1016, the surrogate biomarker is reported to a physician. The physician can use the surrogate biomarker in addition to, or in place of, clinical visits by the patient to assist in the treatment of the patient. Flow of the method 1000 may return to 1002, where additional sensory data is acquired in a continuous or near continuous manner, as described above. Alternatively, the method 1000 may not re-authenticate the patient each time sensory data is acquired. For example, the method 1000 may authenticate the patient only periodically, such as once a day.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the inventive subject matter, including the best mode, and also to enable any person of ordinary skill in the art to practice the embodiments disclosed herein, including making and using any devices or systems and performing any incorporated methods. The patentable scope of the subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the disclosed subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the subject matter herein involved, it is intended that all of the subject matter of the above description or shown in the accompanying drawings shall be interpreted merely as examples illustrating the inventive concepts herein and shall not be construed as limiting the disclosed subject matter.

What is claimed is:

1. A mobile computing device comprising:
   an alarm indicator;
   a motion sensor that detects motion of a person and generates sensory data representing the person's motion; and
   a computer processor configured to:
   extract medically relevant data from the sensory data, the relevant data including one or more features of interest in the sensory data,
   derive one or more surrogate biomarkers from the relevant data, the surrogate biomarkers representative of at least one of a state of a medical condition or a progression of a medical condition of the person, and
   provide a real-time intervention alarm through the alarm indicator when the surrogate biomarkers approach a danger level or threshold that indicates a likelihood of an adverse event occurring to the person, wherein the real-time intervention alarm is provided prior to the occurrence of the adverse event,
   wherein the real-time intervention alarm is based on one or more changes in the relevant data and includes a notification directing the change of a current activity of the person.

2. The device of claim 1, wherein the mobile computing device is a mobile phone configured to be carried by the person, and wherein the motion sensor includes at least one of an accelerometer or a gyroscope that generates the sensory data to represent movements of the person.

3. The device of claim 1, wherein the computer processor is configured to employ one or more machine learning algorithms that identify one or more patterns or trends in the relevant data to derive the surrogate biomarkers.

4. The device of claim 1, wherein the surrogate biomarkers include an estimate of a quantitative clinical score in a medical ranking system.

5. The device of claim 4, wherein the one or more estimates of quantitative clinical scores include at least one of an indication of early onset or a probability of early onset of a disease of the person.

6. The device of claim 1, wherein the computer processor is configured to determine one or more of the features of interest in the sensory data as the relevant data and use the relevant data to identify the person carrying the mobile computing device.

7. The device of claim 1, wherein the medical condition includes at least one of Parkinson's disease, spinal cord injury, multiple sclerosis, cerebral palsy, or cerebellar ataxia.

8. The device of claim 1, wherein the surrogate biomarker is representative of at least one of a degree of activity of the person, gait of the person, sway of the person, tremor of the person, deviation of the person from steady behavior, recovery from perturbation, exercise, wheelchair management, and motorized transport use.

9. The device of claim 1, wherein the computer processor is configured to determine a posture of the person based on the sensory data.

10. The device of claim 1, wherein the computer processor is configured to transmit a report including the surrogate biomarker to one or more of an insurance company, a family member of the person, or a friend of the person.

11. A method comprising:
a mobile computing device measuring sensory data representative of movement of a person using a motion sensor of the mobile computing device;
with the mobile computing device,
extracting the medically relevant data from the sensory data by identifying one or more features of interest in the sensory data;
deriving a surrogate biomarker from the relevant data, wherein the surrogate biomarker represents at least one of a state or a progression of the medical condition of the person; and
providing a real-time intervention alarm through an alarm indicator coupled to the computing device when the surrogate biomarkers approach a danger level or threshold that indicates a likelihood of an adverse event occurring to the person, wherein the real-time intervention alarm is provided prior to the occurrence of the adverse event,
wherein the real-time intervention alarm is based on one or more changes in the relevant data and includes a notification directing the person to change a current activity of the person.

12. The method of claim 11 wherein the mobile computing device is a mobile phone carried by the person and the sensor includes at least one of an accelerometer or a gyroscope that generates the sensory data to represent movements of the person.

13. The method of claim 11, wherein deriving the surrogate biomarker includes employing one or more machine learning algorithms that identify at least one pattern or trend in the relevant data to derive the surrogate biomarker.

14. The method of claim 11, wherein the surrogate biomarker includes at least one of an indication of early onset or a probability of early onset of a disease of the person.

15. The method of claim 11, further comprising determining one or more of the features of interest in the sensory data as the relevant data and identifying the person carrying the mobile computing device using the relevant data.

16. The method of claim 11, further comprising determining a location where the mobile computing device is carried by the person by comparing the relevant data with one or more location signatures associated with different locations wherein the mobile device is carried on the person, the location signatures including one or more of the features of interest of previously acquired sensory data from the sensor when the device is carried in the different locations on the person.

17. The method of claim 11, wherein the medical condition includes at least one of Parkinson's disease, spinal cord injury, multiple sclerosis, cerebral palsy, or cerebellar ataxia.

18. The method of claim 11, wherein the surrogate biomarker is representative of at least one of a degree of activity of the person, gait of the person, sway of the person, tremor of the person, deviation of the person from steady behavior, recovery from perturbation, exercise, wheelchair management, and motorized transport use.

19. The method of claim 11, wherein the surrogate biomarker represents a posture of the person.

20. A non-transitory computer readable storage medium having stored thereon one or more sets of instructions that direct a mobile computing device to:
receive sensory data obtained by a motion sensor in the mobile computing device while the mobile computing device is carried by a person;
extract medically relevant data from the sensory data by identifying one or more features of interest in the sensory data;
derive a surrogate biomarker from the relevant data, wherein the surrogate biomarker represents of at least one of a state of a medical condition or a progression of a medical condition of the person; and
provide a real-time intervention alarm through an alarm indicator coupled to the mobile computing device when the surrogate biomarkers approach a danger level or threshold that indicates a likelihood of an adverse event occurring to the person, wherein the real-time intervention alarm is provided prior to the occurrence of the adverse event,
wherein the real-time intervention alarm is based on one or more changes in the relevant data and includes a notification directing the person to change a current activity of the person.

21. The non-transitory computer readable storage medium of claim 20, wherein the mobile computing device is a mobile phone carried by the person and the motion sensor includes at least one of an accelerometer or a gyroscope that generates the sensory data to represent movements of the person.

22. The non-transitory computer readable storage medium of claim 20, wherein the sets of instructions direct the mobile computing device to:
employ one or more machine learning algorithms that identify at least one of a pattern or a trend in the relevant data, and the surrogate biomarker is based on the at least one of the pattern or the trend.

23. The non-transitory computer readable storage medium of claim 20, wherein the surrogate biomarker includes at least one of an indication of early onset or a probability of early onset of a disease of the person.

24. The non-transitory computer readable storage medium of claim 20, wherein the one or more sets of instructions direct the mobile computing device to determine one or more of the features of interest in the sensory data as the relevant data and to identify the person carrying the mobile computing device based on the features of interest.

25. The non-transitory computer readable storage medium of claim 20, wherein the one or more sets of instructions direct the mobile computing device to determine a location that the mobile computing device is carried by the person by comparing the relevant data with one or more location signatures associated with different locations on the person, the location signatures including one or more of the features of interest of previously acquired sensory data from the sensor when the mobile computing device is carried in the different locations on the person.

26. The non-transitory computer readable storage medium of claim 20, wherein the real-time intervention alarm comprises a fall prevention alarm.

27. The non-transitory computer storage medium of claim 26, further including one or more sets of instructions that direct the mobile computing device to provide the fall prevention alarm to a second person other than the person.

28. The non-transitory computer storage medium of claim 27, wherein the second person other than the person is a pre-identified family member or friend.

29. The non-transitory computer storage medium of claim 27, wherein the second person other than the person is a clinician.

30. The non-transitory computer storage medium of claim 27, wherein the second person other than the person is an emergency personnel.

31. The non-transitory computer storage medium of claim 26, wherein the fall prevention alarm is a tactile alarm.

32. The non-transitory computer storage medium of claim 26, wherein the mobile computing device is fixed to an appendage of the person.

33. The non-transitory computer storage medium of claim 26, wherein the medical condition is a fall risk condition and the medically relevant data comprises acceleration data.

\* \* \* \* \*

UNITED STATES PATENT AND TRADEMARK OFFICE
CERTIFICATE OF CORRECTION

| | |
|---|---|
| PATENT NO. | : 10,750,977 B2 |
| APPLICATION NO. | : 15/868187 |
| DATED | : August 25, 2020 |
| INVENTOR(S) | : Konrad P. Kording, Mark V. Albert and Andrew Levien |

It is certified that error appears in the above-identified patent and that said Letters Patent is hereby corrected as shown below:

In the Specification

Column 1, Line 27, add the following paragraph:
--STATEMENT REGARDING FEDERALLY SPONSORED RESEARCH OR DEVELOPMENT
This invention was made with government support under grant number P01 NS044393 awarded by the National Institutes of Health. The government has certain rights in the invention.--

Signed and Sealed this
Seventh Day of November, 2023

Katherine Kelly Vidal
*Director of the United States Patent and Trademark Office*